(12) United States Patent
Vidalis

(10) Patent No.: US 11,850,304 B2
(45) Date of Patent: Dec. 26, 2023

(54) INTRAVAGINAL FORMULATION

(71) Applicant: The Materia Company Limited, San Gwann (MT)

(72) Inventor: Matthaios Vidalis, San Gwann (MT)

(73) Assignee: THE MATERIA COMPANY LIMITED, San Gwann (MT)

( * ) Notice: Subject to any disclaimer, the term of this patent is extended or adjusted under 35 U.S.C. 154(b) by 0 days.

(21) Appl. No.: 17/042,555

(22) PCT Filed: Mar. 28, 2019

(86) PCT No.: PCT/EP2019/057925
§ 371 (c)(1),
(2) Date: Sep. 28, 2020

(87) PCT Pub. No.: WO2019/185834
PCT Pub. Date: Oct. 3, 2019

(65) Prior Publication Data
US 2021/0030674 A1 Feb. 4, 2021

(30) Foreign Application Priority Data
Mar. 29, 2018 (EP) ..................... 18165128

(51) Int. Cl.
| | |
|---|---|
| *A61K 9/12* | (2006.01) |
| *A61K 9/00* | (2006.01) |
| *A61K 9/14* | (2006.01) |
| *A61K 31/4164* | (2006.01) |
| *A61K 31/4706* | (2006.01) |
| *A61K 31/69* | (2006.01) |

(Continued)

(52) U.S. Cl.
CPC ............ *A61K 9/124* (2013.01); *A61K 9/0034* (2013.01); *A61K 9/12* (2013.01); *A61K 9/143* (2013.01); *A61K 9/145* (2013.01); *A61K 9/146* (2013.01); *A61K 9/148* (2013.01); *A61K 31/4164* (2013.01); *A61K 31/4706* (2013.01); *A61K 31/69* (2013.01); *A61K 33/22* (2013.01); *A61P 15/00* (2018.01); *A61P 15/02* (2018.01)

(58) Field of Classification Search
None
See application file for complete search history.

(56) References Cited

U.S. PATENT DOCUMENTS

| | | | |
|---|---|---|---|
| 3,936,402 A | 2/1976 | Keegan et al. | |
| 4,001,151 A * | 1/1977 | Keegan | A61K 8/8158 523/120 |

(Continued)

FOREIGN PATENT DOCUMENTS

| | | |
|---|---|---|
| CN | 101181636 A | 5/2008 |
| WO | 2017/069721 A1 | 4/2017 |

OTHER PUBLICATIONS

Fadanelli et al. (abstract for "Combining bisphosphonates with hormone therapy for postmenopausal osteoporosis", Treat Endocrinol. vol. 3(6) (2004) p. 361-369) (Year: 2004).*

(Continued)

*Primary Examiner* — Sin J Lee
(74) *Attorney, Agent, or Firm* — WOMBLE BOND DICKINSON (US) LLP

(57) ABSTRACT

An intravaginal formulation comprising a dry powder composition and propellant(s) and the apparatus capable of delivery intravaginally a dry powder composition.

12 Claims, 8 Drawing Sheets

(51) Int. Cl.
*A61K 33/22* (2006.01)
*A61P 15/00* (2006.01)
*A61P 15/02* (2006.01)

(56) References Cited

U.S. PATENT DOCUMENTS

| | | | | |
|---|---|---|---|---|
| 2004/0005345 | A1* | 1/2004 | Pauletti | A61P 19/10 514/102 |
| 2009/0297441 | A1* | 12/2009 | Canham | A61K 49/06 424/9.4 |
| 2011/0250626 | A1* | 10/2011 | Williams | C12Q 1/34 106/4 |
| 2012/0111324 | A1* | 5/2012 | Kraft | A61K 9/0075 128/203.15 |
| 2013/0317104 | A1* | 11/2013 | Batcheller | A61K 45/06 560/180 |
| 2014/0241998 | A1 | 8/2014 | Friedman et al. | |
| 2015/0157674 | A1* | 6/2015 | Rishi | A61K 36/23 424/725 |
| 2015/0368470 | A1* | 12/2015 | Huh | C08L 21/00 524/71 |
| 2019/0091279 | A1* | 3/2019 | Chemtob | A61P 29/00 |

OTHER PUBLICATIONS

Bermudez-Bejarano et al. ("Prophylaxis and antibiotic therapy in management protocols of patients treated with oral and intravenous bisphosphonates", Journal of Clinical and Experimental Dentistry, vol. 9(1) (2017), p. 141-149) (Year: 2017).*

Na Wu, et al. (Correspondence Yong Gan), "Spray-dried powders enhance vaginal siRNA delivery by potentially modulating the mucus molecular sieve structure", International Journal of Nanomedicine, XP055486052, Aug. 1, 2015, pp. 5383-5396, Auckland, NZ.

Omar F Rabeea, et al., "Universal Vaginal Applicator for the Uniform Distribution of Vaginal Gel and Cream Formulations: A Magnetic Resonance Imaging Study", Journal of Obstetrics and Gynaecology Canada, XP055486121, Jan. 2014, pp. 42-50, vol. 36, No. 1.

Himmat Singh Johal, et al., "Advanced topical drug delivery system for the management of vaginal candidiasis", Drug Delivery, 2016, pp. 550-563, vol. 23, No. 2.

International Search Report for PCT/EP2019/057925 dated May 21, 2019 (PCT/ISA/210).

Written Opinion for PCT/EP2019/057925 dated May 21, 2019 (PCT/ISA/237).

* cited by examiner

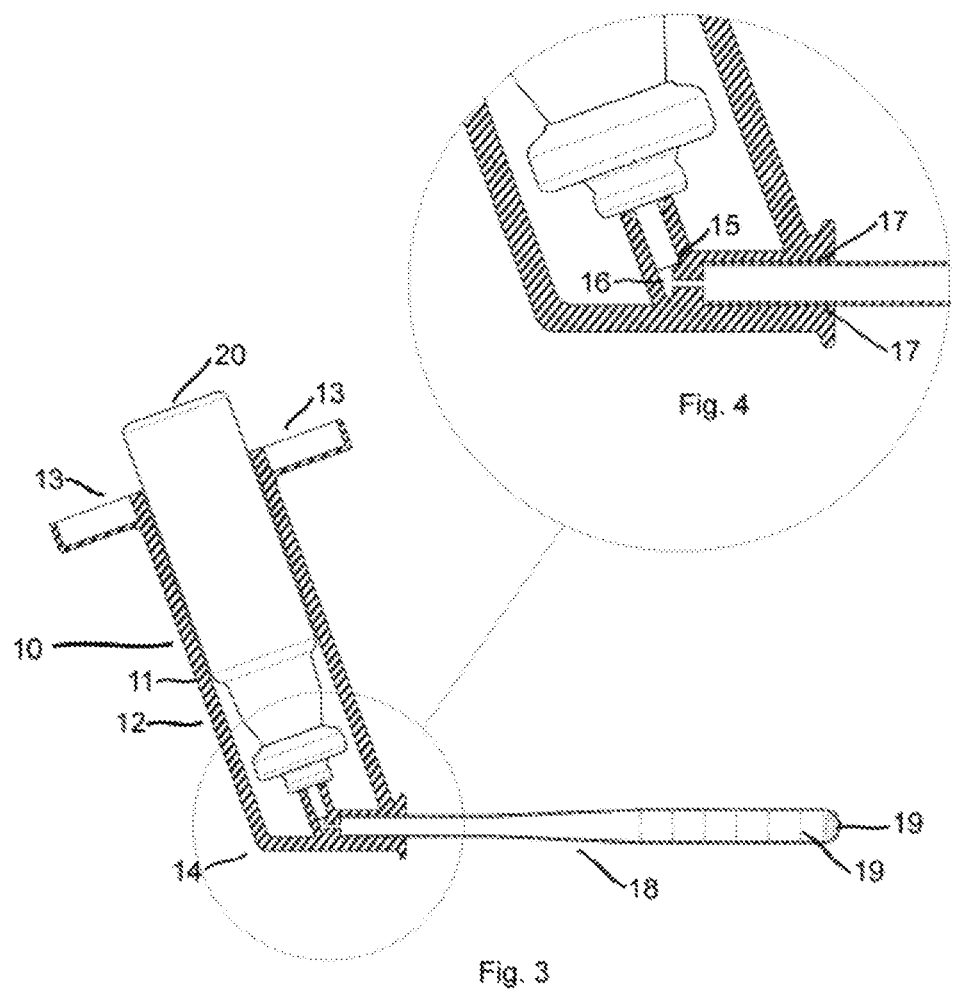

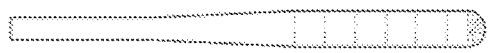
Variation A
Variation B
Fig. 10
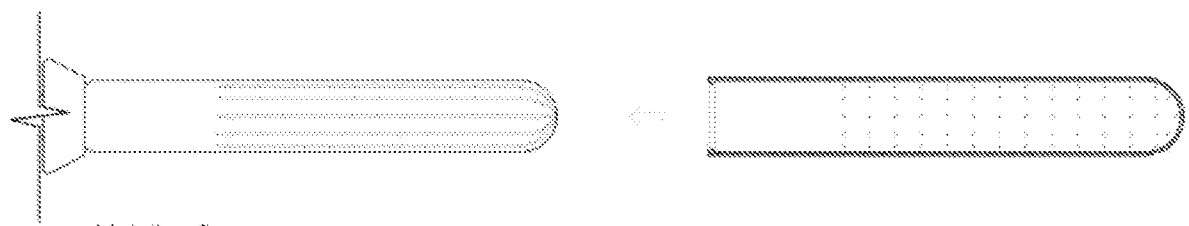
Variation C
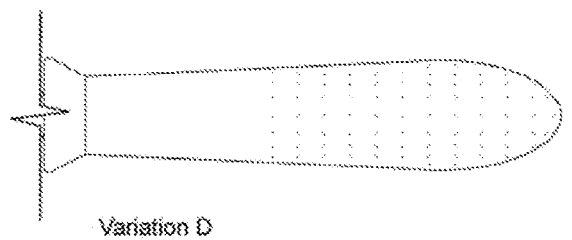
Variation D
Fig. 11

INTRAVAGINAL FORMULATION

FIELD OF THE INVENTION

The present invention relates to an intravaginal formulation, comprising a dry powder composition and at least one propellant, the process for preparing, the suitable apparatus and its use, as defined by the claims.

BACKGROUND OF THE INVENTION

Vaginal products are marketed under forms of tablets, capsules, pessaries and semi-solid formulations such as foams, creams, ointments and gels. These products are available as prescription and over the counter (OTC) products for the treatment and prevention of vaginal infections such as bacterial vaginitis, vulvovaginitis, contraceptives, dryness or for cosmetic use. Conventional dosage formulations are predominantly associated with poor vaginal mucosa distribution and retention, mostly due to the self-cleaning action, mucus producing properties of the vaginal canal. Several in vivo studies have pointed out limitations of currently used vaginal formulations in accomplishing the aforementioned prerequisites for successful therapy. These limitations have been associated with several factors, including the anatomical features of the vagina such as the numerous collapsed rugae representing an extensive surface area and the S shape of the vaginal canal, the volume of formulation applied, the variable amount of vaginal fluid and the variety of the degree of interference of deambulation or sexual intercourse. For a general review of vaginal applications see also Himmat S. Johal et. All, Drug Delivery 23(2), 550-563 (2016).

Among the currently marketed dosage forms, semi-solids and in particular gels, have been considered the preferred therapeutic strategy due to their ability to spread and disperse across most of the vaginal tract surface. Furthermore, it has also been stated by clinical experience that patient compliance and overall satisfaction is higher for semi-solid formulations.

Conventional vaginal applicators with a single hole do not distribute vaginal formulations homogenously and do not cover the entire vaginal and cervical mucosa. Since the mode of action of conventional gels depends on poor vaginal mucosa distribution new applicators have been designed by Rabeea F. Omar et all, J Obstet Gynaecol Can. 36(1), 42-50 (2014).

In view of the above state of art, the present inventors have come up with a formulation for intravaginal administration of a dry powder composition which provides relatively better effect than other dosage forms known such as vaginal gels, pessaries, suppositories, capsules or tablets. Further, the novel mode of delivery achieves better distribution of the composition into the vaginal tract.

BRIEF DESCRIPTION OF THE FIGURES

FIG. 3. A side cross-sectional view of an apparatus suitable for intravaginal delivery comprising a housing, according to the present invention.

FIG. 4. An enlarged view side cross-sectional view of the product release chamber of FIG. 3.

FIG. 10 Variations of a single-use elongated tube/probe

FIG. 11 Variations of a multi-use elongated tube/probe and suitable single-use cap with openings.

DETAILED DESCRIPTION OF THE INVENTION

Figure 1:
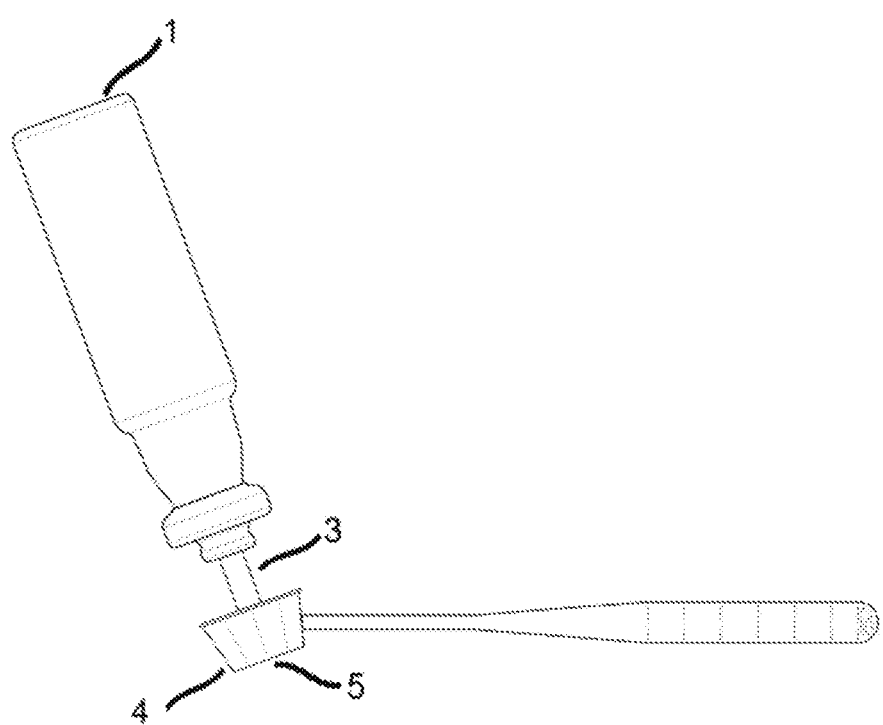
FIG. 1. A side view of an apparatus suitable for intravaginal delivery without a housing, according to the present invention.

The present invention relates to an intravaginal formulation, comprising a dry powder composition and at least one propellant and its method of preparing thereof.

The present invention further relates to a pressurized container comprising the intravaginal formulation as claimed and the apparatus comprising the pressurized container with a valve and an at least partially covered with openings elongated tube with an open and a closed end.

The present invention further relates to the intravaginal formulation as claimed, wherein the dry powder composition comprises an active agent.

The present invention further relates to the intravaginal formulation as claimed, wherein the dry powder composition comprises an herbal extract.

The present invention further relates to the intravaginal formulation as claimed, which is insufflated into the body cavity, for use in the treatment and/or prevention of pathological diseases associated with the vagina by topical administration of an active or a non-active agent or mixtures thereof, to the vaginal and/or the female urogenital tract to the vagina or the cervix or the uterus.

The present invention further relates to the use of the intravaginal formulation as claimed, for the manufacturing of a medicament for the treatment and/or prevention of pathological diseases associated with the vagina by topical administration of an active or a non-active agent or mixtures thereof, to the vaginal and/or the female urogenital tract to the vagina or the cervix or the uterus.

A vaginal disease is a pathological condition or a disorder that affects part or all the vagina. Some of the vaginal diseases include but are not limited to inflammatory diseases such as, acute vaginitis, acute vulvovaginitis, subacute vaginitis, subacute vulvovaginitis, chronic vaginitis, chronic vulvovaginitis, vaginal ulcerations, non-infectious vuvlovaginitis, non-infectious vaginitis and infectious diseases, such as bacterial vaginitis, bacterial vulvovaginitis, fungal vaginitis, fungal vulvovaginitis, vulvovaginal candidiasis, vaginal candidiasis, aerobic vaginitis, aerobic vulvovaginitis.

In addition the present invention can be used for the treatment and/or prevention of sexually transmitted diseases, such as, gonorrhea (*Neisseria gonorrheae* infection), *chlamydia* (*Chlamydia trachomatis* infection), trichomoniasis (*Trichomonas vaginalis* infection), herpes genitalis (Herpes simplex viral {HSV} infection), Human Papilloma Virus (HPV) infection, genital warts, pinworm vaginal infection, syphilis (*Treponema palladium* infection), post-menopausal atrophic vaginitis, atrophic vulvovaginitis, vaginal dryness, vaginal itching, vaginal sores, vaginal lumps, vaginal cysts, dyspareunia, leukorrhea, vaginal discharge and hormonal supplementation of luteal phase during pregnancy, assisted reproduction technologies {In vitro Fertilization (IVF), Intra Uterine Insemination (IUD)}, secondary amenorrhea, vaginal bleeding, prevention of preterm labor in women with short cervix or high risk of abortion, reduction of preterm contractions (Tocolytics), contraception, vaginal cancer (squamous cell carcinoma, adenocarcinoma, sarcoma, melanoma) and more.

The present invention and its delivery system designed for vaginal application, relates to topical administration intravaginally of a dry powder composition which subsequently promotes maximum distribution in the human vaginal tract, compared to marketed products currently available.

Since known formulations are proven antiquate, the new composition seeks enhanced delivery and retention in the vaginal canal, solubility and vaginal distribution utilizing the physiological features of the environment (fluid amount, composition, pH etc.), while subsequently recovering and fortifying a healthy vaginal ecosystem.

Utilizing such a novel administration amplifies dispersion of ingredients to all the sites of the vaginal canal, as one can overcome the anatomic particularities of the urogenital tract, due to the specifics of product formulation and means of application, under the spectrum of effective vaginal treatment.

The efficacy of the invention mainly relies on the ability of the respective composition to spread over the entire vaginal surface upon administration and to be retained for an adequate period, enough to exert its therapeutic capacity in an effective manner.

The present invention provides for administration or application of the intravaginal formulation by insufflating into the body cavity a non-active and/or an active agent to the vaginal and/or urogenital tract of a female, including, e.g., the vagina, cervix, or uterus of a female.

The present invention relates to an intravaginal formulation comprising substantially a dry powder composition and at least one propellant, wherein the dry powder composition comprises an active agent.

The present invention relates to an intravaginal formulation comprising substantially a dry powder composition and at least one propellant, wherein the dry powder composition comprises an herbal extract.

Preferably, the present invention relates to the intravaginal formulation as claimed, wherein the dry powder composition comprises an active agent and/or an herbal extract and/or non-active agents. More preferably, the present invention relates to the intravaginal formulation as claimed, wherein the dry powder composition further comprises a pharmaceutically acceptable excipient. More preferably, the present invention relates to the intravaginal formulation as claimed, wherein the dry powder composition further comprises at least one thickening agent.

The term "active agent" in the context of the present invention, is a chemical or biological agent capable of activity, for prevention or treatment of diseases associated with the vaginal tract. The active agents include but are not limited to pharmaceutically acceptable small molecules used in vaginal infections and are well-known, first-line antibiotics, probiotics, prebiotics, pH-regulators and peptide/proteins such as Elagolix, Relugolix, Linzagolix, antibodies, vaccines and gene-based therapeutics. In detail, anti-infectives and antiseptics, like, antibiotics, such as Azithromycin, Clarithromycin, Natamycin, Ciclopirox Olamine, Erythromycin, Telithromycin, Pristinamycin, Nystatin, Nifuratel, Caspofungin, Anidulafungin, Mepartricin, Terbinafine, Terbinafine hydrochloride, Tolnaftate, Candicidin, Amphotericin B, Flucytosine, Clindamycin, Clindamycin phosphate, Neomycin, Neomycin sulfate, Polymyxin B sulfate, Rifaximin, Tetracycline and Oxytetracycline, Mepatricin, Solithromycin, Sitafloxacin, Mupirocin Base, Mupirocin Calcium, arsenic compounds, such as Acetarsol, quinoline derivatives, such as Broxyquinoline, Diiodohydroxyquinoline, Dequalinium chloride, Dequalinium bromide, Dequalinium iodide, Dequalinium acetate, Dequalinium undecenoate, Chlorquinaldol, Clioquinol, Oxyquinoline, organic acids, such as Lactic acid, Acetic acid, Ascorbic acid, Lactoserum, imidazole derivatives, such as Metronidazole, Clotrimazole, Fenticonazole, Fenticonazole nitrate, Flutrimazole, Sertaconazole, Tioconazole, Econazole, Econazole nitrate, Isoconazole, Ketoconazole, Miconazole, Miconazole nitrate, Butoconazole, Oxiconazole, Omoconazole, Azanidazole, Propenidazole, Sulconazole, Tinidazole, Ornidazole, Nimorazole, Azanidazole, triazole derivatives, such as Terconazole, Voriconazole, Itraconazole, Fluconazole, Posaconazole and other such as Clodantoin, Policresulene, Inosine, Furazolidone, Povidone iodine, Octenidine hydrochloride, Octenidine dihydrochloride, Phenoxyethanol, Benzalkonium cloride, Aluminum potassium sulphate, Hexetidine, Chlorhexidine, Boric acid, Hydrogen peroxide, Anti-viral molecules, such as Tenofovir, Tenofovir disoproxil, Abacavir, Dapivirine, Zidovudine, Valacyclovir, Maraviroc, Acyclovir, Brivudin, Cidofovir, Famciclovir, Penciclovir, Foscarnet, Ganciclovir, Imiquimod, Emtricitabine, Idinavir, Ritonavir, Imiquimod, Fomivirsen, Foscarnet, Ganciclovir, Valganciclovir, Oseltamivir, Zanamivir, Adefovir, Entecavir, Atazanavir, Raltegravir and anesthetics such as Lidocaine, Prilocaine, Cinchocaine can be used.

Active gents comprise and not limited to selective phosphodiesterase type 5 inhibitor such as Sildenafil, Tadalafil, Vardenafil, Avanafil and cancer chemotherapy active agents such as Gemcitabine, Cisplatin, Bleomycin, Topotecan, Irinotecan, Adavosertib, Carboplatin, Oxaliplatin, Paclitaxel, Capecitabine, Fluda rabine, Cyclophosphamide, 5-Fluorouracil. Other active agent include but are not limited to aromatase inhibitors such as Anastrozole, Letrozole, Exemestane, Vorozole, non-steroidal anti-inflammatory drugs (NSAIDs) and opioids such as Benzydamine hydrochloride, Naproxen, Ibuprofen, Flunoxaprofen, Meloxicam, Morphine, Oxycodone and corticosteroids such as Hydrocortisone, Methylprednisolone, Betamethasone valerate, Prednisone, Fluocinonide. Antimalarials such as Quinidine, Artesunate, Amodiaquine, Sulfadoxine, Pyrimethamine. Further PARP inhibitors can be used such as Olaparib, Rucaparib, Niraparib, Talazoparib as active agents.

Other active agent include but are not limited to sex hormones, steroids such as Tibolone and steroid hormons such as Estetrol, uterotonics and genital system modulators, like prostaglandins such as Misoprostol, Dinoprost, Dinoprostone, Gemeprost, like progestogens, such as Hydroxyprogesterone, Progesterone, Medroxyprogesterone, Gestonorone, like estrogens, such as Estriol, Estriol succinate, Estradiol, Estradiol acetate, Estradiol hemihydrate, Ethinylestradiol, Oxytocin, Promestriene, Diethylstilbestrol, Dehydroepiandrosterone, Tibolone, conjugated estrogens or anti-progestogens such as Mifepristone, Lilopristone, Onapristone, Ulipristal acetate, Aglepristone and progestins, such as Etonogestrel, Norethisterone, Norethisterone acetate, Medroxyprogesterone acetate, Megestrol acetate, Hydroxyprogesterone caproate, Cyproterone acetate, Dydrogesterone, Allylestrenol, Norgestimate, Levonorgestrel, Desogestrel, Drospirenone, Gestodene. Also, monoclonal antibodies such as anti-HIV antibodies such as B-12 and P2G12 and chemotherapy agents such as Avelumab, Bevacizumab, Atezolizumab, Pembrolizumab, Durvalumab, Tremelimumab, Ipilimumab and Nivolumab, can be used. Bacterium such as *Propionibacterium acnes* can be used as active agents.

Further selected from the group of contraceptives and spermicides, selective estrogen receptor modulators (SERM), tocolytics, natural antimicrobials, peptides and toxins, such as Nonoxynol-9, Benzalkonium chloride, Sodium cholate, Octoxynol-9, Glyminox, Ospemifene, Bazedoxifene, Ormeloxifene, Raloxifene, Tamoxifen, Bateriocins, Subtilosin, Lauramide arginine ethyl ester, Atosiban, Terbutalin, Nifedipine Glycerol laurate, Lactocin 160, Retrocyclin (RC-101), Cathelicidin, can be used.

In addition other molecules can be used such as Polycarbophil, Carbopol, Silica, Polysaccharides, Active Hexose Correlated Compound, Hyaluronic acid, Bisabolol, Allantoin, Silver salts such as Silver nitrate, Oxybutynin, Calcium lactate, Poly-L-lysine, Glycerine, Metformin hydrochloride, Melatonin, Pilocarpine dendrimers such as Sulfonate-terminated anionic poly(lysine)-based dendrimers (SPL7013), Polyanionic carbosilane dendrimers and combinations thereof. Vitamins such as Vitamin A, Vitamin B, Vitamin B3, Vitamin C, Vitamin E, Vitamin D and derivatives thereof, Panthenol and combinations thereof can be used. In addition, inositol, alpha-lipoic acid, n-acetyl-cysteine, Lactose-rum and medical cannabis such as CBD, THC, or any other cannabis ingredients, alone or in combinations can be used.

The term "herbal extract" in the context of the present invention, is extract of herbs and other natural plant ingredients such as majorana, melissa, chaste tree fruits, tea tree oil, kunecatechins, extracts of tea leaves, *Aloe barbadensis*, *Aloe vera*, Algae such as Padina Pavonica, Sesame seed oil, cinnamon oil, and essential oils, *Zataria multiflora* extract, Brazilian pepper tree extract, *Calendula officinalis* extract, *Berberis vulgaris* extract, *Portulaca oleracea* (purslane), *Opuntia ficus*, *Vanilla tahitensis*, *Cinchona officinalis*, *Punica granatum*, *Flos salis*, *Matricaria chamomilla* extract, *Aloe vera barbadensis* extract, *Myrtus communis* extract, Witch hazel extract, *Echinacea angustifolia* extract, Cranberry extract, Menthol, Propolis extract, Phytoestrogens (Isoflavones, Lignan), Genistein, Eugenol, Cinnamaldehyde, Quercetin, Epicatechin, Thymol, Carvacrol, Reservatol, Ellagitannins, Proanthocyanidins, Polyphenon E and their combination thereof.

The term "dry powder composition" typically refers to a powder composition that is—amongst other features—characterized by its residual moisture content, which is preferably low enough to prevent the formation of aggregates that would reduce or inhibit the flowability of the powder, as well as block the apparatus' valve during discharge. As used herein, the term "residual moisture content" typically refers to the total amount of water present in the dry powder composition. Said total amount of residual moisture in the dry powder composition is determined using any suitable method known in the art. For example, methods for determining the residual moisture content comprise the Karl-Fischer-titrimetric technique or the thermal gravimetric analysis (TGA) method. In a preferred embodiment, the residual solvent comprised in the dry powder composition is water or an essentially aqueous solution and the residual moisture content corresponds to the residual water content of the dry powder composition, which is determined by the Karl-Fischer-titrimetric technique. Without being bound by any theory, the low residual moisture content of the inventive intravaginal formulation comprising the dry powder composition is expected to contribute to its excellent storage stability preventing product degradation.

Preferably, the residual moisture content of the dry powder composition according to the invention is 15% (w/w) or less, more preferably 10% (w/w) or less, even more preferably 9% (w/w), 8% (w/w), 7% (w/w), 6% (w/w) or 5% (w/w). In a preferred embodiment, the residual moisture content of the dry powder composition is 5% (w/w) or less, preferably 4% (w/w) or less. In a particularly preferred embodiment, the residual moisture content is 7% (w/w) or less. In a further preferred embodiment, the residual moisture content of the powder composition in the range from 0% to 15% (w/w), from 0% to 10% (w/w), from 0% to 7% (w/w), from 0% to 5% (w/w), from 0% to 4% (w/w), from 3% to 6% (w/w) or from 2% to 5% (w/w).

Preferably, the residual moisture content of the intravaginal formulation according to the invention is 15% (w/w) or less, more preferably 10% (w/w) or less, even more preferably 9% (w/w), 8% (w/w), 7% (w/w), 6% (w/w) or 5% (w/w). In a preferred embodiment, the residual moisture content of the dry powder composition is 5% (w/w) or less, preferably 4% (w/w) or less. In a particularly preferred embodiment, the residual moisture content is 7% (w/w) or less. In a further preferred embodiment, the residual moisture content of the powder composition in the range from 0% to 15% (w/w), from 0% to 10% (w/w), from 0% to 7% (w/w), from 0% to 5% (w/w), from 0% to 4% (w/w), from 3% to 6% (w/w) or from 2% to 5% (w/w).

The term "pharmaceutical acceptable excipients" or "non-active agents" as used herein means components of a pharmaceutical product that is not an active agent as such as, for example, propellants, thickening agents, fillers, lubricants and glidants in the powder mixture for a more efficient delivery, as well as antioxidants, preservatives, anti-microbial agents, surfactants, fatty substances and possibly neutralizing agents.

The non-active agents that are useful in preparing the intravaginal formulation are generally safe and non-toxic.

The expression "at least one" is equivalent to the expression "one or more".

The intravaginal formulation is a propellant gas-driven formulation. The propellant expands upon release to the atmosphere, therefore drives the dry powder composition to the vaginal and/or the female urogenital tract. Various liquefied or non liquefied propellants can be used for the delivery of the dry powder composition intravaginally, deriving but not limited to a selection of one or mixtures of the following, HFA 134a, chlorodifluoroethane (HCFC), chlorofluorocarbons (CFC), difluorotethane (HFC), dimethyl ether, heptafluoropropane (HFC), hydrocarbons (HC), tetrafluoroethane (HFC), compressed air, nitrogen, nitrous oxide, carbon dioxide and helium.

The gases can be employed as "liquefied" propellants can be liquids under pressure which can be tolerated in compressed gas containers. Typical of these liquefied gas propellants used, are fluorinated chlorohydrocarbons and pure hydrocarbons. These propellants separate into a liquid phase and a vapour phase in the compressed gas container. The liquefied propellant gas does not dissolve the dry powder composition. The liquid phase serves as a pressure reserve. If the pressure drops at the moment of spraying, a portion of the liquefied propellant gas immediately evaporates inside the container and the original pressure is completely restored. The pressure remains substantially constant within the compressed gas container from the time of its first use until the container is practically empty. Upon activation of the apparatus, the high vapor pressure of the propellant forces the dry powder composition out through the valve, then the propellant rapidly evaporates forcing the dry powder composition out of the openings of the elongated part to be delivered intravaginally.

In a preferred embodiment 1,1,1,2-Tetrafluoroethane (HFA 134a) with a boiling point of −26.3° C., is a used as a propellant due to non-flammability, low toxicity, ozone-friendly, poor solvency and low solubility.

The gases can be employed as "non liquefied" propellants work in similar ways, providing high pressure to the dry powder composition out through the valve and out of the openings of the elongated part to be delivered intravaginally. Compressed air and Nitrogen cannot be liquefied under pressure, up to 54° C. Carbon Dioxide and Nitrous Oxide can condense under pressure at regular working temperatures and therefore are considered "non liquefied propellants".

In a preferred embodiment nitrogen is used as a propellant.

In a preferred embodiment, the intravaginal formulation comprises at least 80% w/w of a propellant or mixtures thereof.

In a preferred embodiment, the intravaginal formulation comprises 90% w/w or more of a propellant or mixtures thereof.

The term "thickening agent" as used herein means and may be any suitable material which can increase the viscosity of a liquid without substantially changing its other properties. Some thickening agents are gelling agents (gellants), forming a gel, by dissolving in a liquid phase as a colloid mixture that forms a weakly cohesive internal structure. Others act as mechanical thixotropic additives with discrete particles adhering or interlocking to resist strain. Others are fatty substances acting as emulsifiers. More preferably, the "thickening agent" forms a gel or a mucilage or an emulsion mass upon contact with an aqueous medium. Formation of a gel or a mucilage or an emulsion mass relieves irritation of mucous membranes by forming a protective layer. Those substances include but are not limited to acacia, agar, alginic acid, aliphatic polyesters, ammonium, calcium, sodium, potassium alginate, arabic gum, attapulgite, bentonite, calcium polycarbophil, polycarbophil and polyacrylic acid, carragenan in various grades and types, ceratonia, cholesterol, copovidone, dextrins, dibutyl phthalate, dibutyl sebacate, diethyl phthalate, dimethyl phthalate, ethylene vinyl acetate, gelatin, glyceryl behenate, guar gum, hectorite, inulin, mucin, saponite, shellac, hyaluronic acid and its salts, pectin, poloxamers, polydextrose, polyethylene oxide, polyquaterniums, polyvinyl acetate, propylene glycol alginate, povidone, sulfobutyl ether β-cyclodextrin, tragacanth, trehalose, triacetin, xanthan gum, aluminum monostearate, cetostearyl alcohol, cetyl alcohol, stearyl alcohol, glyceryl monooleate, glyceryl palmitostearate, polyoxyethylene castor oil derivatives, polyoxyethylene stearates, polyoxyl glycerides and sorbitan fatty acid ester and combinations thereof.

For the scope of the present invention the "thickening agent" is introduced dry, in order to take advantage of the vaginal mucosa's humidity, so to adhere to the vaginal walls creating an in-situ gel or mucilage or emulsion, aiming to the retention and active pharmaceutical ingredient delivery topically.

Regarding the pH value of the area, the physiological vaginal pH ranges from 3.5-4.5 and in cases under infection, such as bacterial vaginitis, aerobic vaginitis and trichmoniasis, the value is shown to be higher than 4.5 and 5 respectively. Despite the presence of electrolytes in the vaginal mucosa, where some thickening agents are incompatible with, the desired gel or mucilage or emulsion can still easily form on spot, when the thickening agents are delivered in dry powder form.

In a preferred embodiment, due to their excellent properties, a combination of polycarbophil and polyacrylic acid, such as Carbomer 974P, is used.

The term "filler" in the context of the present invention are substances used, either as dispersing agents for a better delivery of the active(s) involved, either considering the possible thickening increasing properties of pharmaceutically acceptable fillers or diluents include but are not limited to cellulose, ethyl cellulose, corn starch, pregelatinized starch, starch, maize starch, hydroxypropyl starch, hydroxypropyl cellulose (regular & low substituted), microcrystalline cellulose, methyl cellulose, hydroxyethyl cellulose, hydroxymethyl cellulose, hypromellose, sodium and calcium carboxymethyl cellulose and lactose, polyols and sugar alcohols such as mannitol and sorbitol.

The term "lubricant" in the context of the present invention, is taken to mean that an ingredient added to prevent adhesion and reduce inter-particle friction. Lubricant of present invention includes but not limited to talc, magnesium stearate, stearic acid, sodium stearyl fumarate and derivatives thereof.

The term "glidant" in the context of the present invention, is taken to mean that an ingredient which enhance product flow by reducing inter-particulate friction. Glidant can be used in present invention includes but not limited to silicon di-oxide, colloidal silicon dioxide and there derivatives thereof. It is available under several brand names like AEROSIL® and CAB-O-SIL®.

Antioxidant protection to the composition, deriving but not limited to a selection of one or more of the following substances ascorbic acid, ascorbyl palmitate, butylated hydroxyanisole, butylated hydroxytoluene, citric acid, tocopherols, edetic acid and edetates, erythorbic acid, fumaric acid, malic acid, methionine, pententic acid, potassium and sodium metabisulfite, propionic acid and salts, propyl gallate and various alkyl gallates, sodium ascorbate, sodium formaldehyde sulfoxylate, sodium metabisulfite, sulfite and thiosulfate, sorbic acid, sulfur dioxide, vitamin E d-α-tocopheryl polyethylene glycol succinate.

The term "neutralizing agents" in the context of the present invention deriving but not limited to a selection of one or more of the following substances, sodium and potassium hydroxide, β-alanine, lysine, arginine, histidine, low molecular weight amines and alkanolamines (diisopropanolamine, coconut alkylamine), aminomethyl propanol, polyoxyethylenes, triethanolamine, tromethamine, tetrakis-2-hydroxypropyl ethylenediamine.

Preferably, the dry powder composition of the intravaginal formulation comprises a plurality of particles. Therein, the term "particle" typically refers to an individual solid particle of the dry powder composition. The individual particles of the intravaginal dry powder composition according to the invention are preferably physically separated from each other, i.e. the individual particles that constitute the dry powder may be in lose and reversible contact with each other (as opposed to an irreversible link between individual particles). Preferably, the term "particle" refers to the smallest physical entity of the dry powder composition. The particles of the dry powder composition do preferably not stick to each other. The particulate nature of the dry powder composition contributes to the characteristics of the inventive intravaginal formulation, e.g. succeeding good dispersion and avoid blocking the apparatus valve, due to the low particle size value of the materials used.

In a preferred embodiment, the dry powder composition as described herein the plurality of individual particles of the dry powder composition according to the invention is characterized by a size distribution, wherein the size of individual particles may be the same or different from each other. Typically, the size of the particles of a dry powder composition is characterized by a Gaussian distribution or a quasi-Gaussian distribution.

A powder sample is dispersed and stirred in a suitable liquid called a dispersion medium to form a suspension. Dispersing aids (wetting agents, stabilisers) and/or mechanical forces e.g. agitation, sonication, could be applied for deagglomeration or deaggregation of clusters and stabilisation of the dispersion. For these liquid dispersions, a recirculating system can be used, consisting of an optical measuring flow cell illuminated with laser beams, a dispersion bath equipped with stirrer and ultrasonic elements, a pump, and tubing.

The detected scattered light from impact with the particles, is measured by an appropriate optical detector array and the results of this measurement are then used to calculate the intensity distribution of the resulting diffracted light and the particle distribution of the sample on the basis of Fraunhofer's diffraction theory and Mie's scattering theory. The particle-size distribution data are reported as percentage of the total amount by volume of the particles having a specific size.

Preferably, the dry powder composition according to the invention is characterized by a volume weighted particle size distribution as determined, for instance, by static light scattering techniques, such as laser diffraction, or by using a cascade impactor. In a volume weighted distribution, the contribution of each particle in the dry powder composition relates to the volume of that particle.

Preferably, more than 90% of the total amount by volume of each of the ingredients employed in the dry powder composition particles have a size of less than 150 μm, when measured by Malvern particle size analyzer. Preferably, more than 90% of the total amount by volume of the dry powder composition particles according to the invention have a size of equal to or less than 150, 125, 100, 75, 60, 50, 40, 30, 20, 10 or 1 μm.

Preferably, more than 90% of the total amount by volume of the dry powder composition particles have a size of equal to or less than 150 μm.

Preferably, more than 90% of the total amount by volume of the dry powder composition particles have a size of equal to or less than 80 μm.

More preferably, more than 90% of the total amount by volume of the dry powder composition particles have a size of equal to or less than 50 μm.

Preferably, the intravaginal formulation as claimed, comprises more than 90% of the total amount by volume of the dry powder composition particles have a size of equal to or less than 150 μm.

Preferably, the intravaginal formulation as claimed, comprises more than 90% of the total amount by volume of the dry powder composition particles have a size of equal to or less than 80 μm.

More preferably, the intravaginal formulation as claimed, comprises more than 90% of the total amount by volume of the dry powder composition particles have a size of equal to or less than 50 μm.

Other known particle size technique can be used but not limited to air jet sieve. The air jet sieve is a sieving machine for single sieving, i.e. for each sieving process only one sieve is used. A system that uses a single sieve at a time is referred to as air-jet sieving. The sieve itself is not moved during the process. It uses the same general sieving methodology as the dry sieving method, but with a standardised air jet replacing the normal agitation mechanism.

The material on the sieve is moved by a rotating jet of air: A vacuum cleaner which is connected to the sieving machine generates a vacuum inside the sieving chamber and sucks in fresh air through a rotating slit nozzle. When passing the narrow slit of the nozzle the air stream is accelerated and blown against the sieve mesh, dispersing the particles.

Above the mesh, the air jet is distributed over the complete sieve surface and is sucked in with low speed through the sieve mesh. The finer particles are transported through the mesh openings into the vacuum cleaner or, optionally, into a cyclone.

In the sonic-sifter method, a nest of sieves is used, and the test sample is carried in a vertically oscillating column of air that lifts the sample and then carries it back against the mesh openings at a given number of pulses per minute.

Results can be expressed by converting the raw data into a cumulative mass distribution, and if desired to express the distribution in terms of a cumulative mass undersize, the range of sieves used must include a sieve through which all the material passes.

A process for preparing an intravaginal formulation comprising the steps of:
  i. preparing a dry powder composition wherein more than 90% of the total amount by volume of the dry powder particles have a size of less than 150 μm,
  ii. loading the dry powder composition into a container and at least one propellant under a predetermined pressure,
  iii. sealing the pressurized container.

In another embodiment the process of preparing an intravaginal formulation comprising the steps of:
  i. preparing a dry powder composition wherein more than 90% of the total amount by volume of the dry powder particles have a size of less than 50 μm,
  ii. loading the dry powder composition into a container and at least one propellant under a predetermined pressure,
  iii. sealing the pressurized container.

Preferably, the process of preparing an intravaginal formulation comprises step ii) loading the dry powder composition into the container and the at least one propellant under a predetermined constant pressure.

Preferably, the process of preparing an intravaginal formulation comprises checking that more than 90% of the total amount by volume of the dry powder composition particles have a size of less than 150 μm, or more preferably less than 100 μm or more preferably less than 50 μm.

Preparing a dry powder composition is required and is achieved by conventional means to prepare a free-flowing dry powder composition with an acceptable content uniformity and appropriate particle size. The preparation can comprise well known steps, such as dry powder mixing, dry granulation, wet granulation, fluidized hot melt granulation, hot melt extrusion, roller compaction, spray drying, spray congealing, freeze drying and fluid bed granulation.

Other manufacturing process techniques that can be applied include but are not limited to a selection of one or combinations of the following mixtures or techniques, such as liposomes & pro-liposomes, lipospheres, lipid-coated particles, solid lipid nanoparticles, nanostructured lipid carriers, microparticles & microspheres, liquid crystals, solid dispersions, thin film freezing, lyophilization, nanofibers and microfibers.

Reduction of the particle size is optional. Preferably, a non active agent or an active ingredient or mixtures thereof wherein more than 90% of the total amount by volume of the particles of the material or their mixtures thereof, have a size of more than 150 μm, is further processed for reduction of the particle size. More preferably, a non active agent or an active ingredient or mixtures thereof wherein more than 90% of the total amount by volume of the particles of the material or their mixtures thereof, have a size of more than 50 μm, is further processed for reduction of the particle size. Reduction of particle size is achieved via comminution, or a mechanical process of reducing the size of particles which includes any one or more of cutting, chipping, crushing, grinding, milling, micronizing, and trituration.

In a preferred embodiment, the intravaginal formulation, as described in the claims, is packed in a pressurized container, which can be achieved by measures that are commonly known in the art, such as with the addition of a propellant gas, by a container with moveable piston, or a container having several compartments. Preferably, the pressure in the pressurized container is achieved by application of the appropriate pressure of the respective propellant gas or mixtures thereof.

In a preferred embodiment, the pressurized container is a multidose and/or single dose container. The container can be made of but not limited to metal, such as aluminum, plastic and glass, plain or coated with plastic material(s).

The present invention relates to an apparatus suitable for delivery of the intravaginal formulation, as described in the claims, comprising a pressurized container with a valve and an at least partially covered with openings elongated tube with an open and a closed end. The periphery of said elongated tube being free of sharp edges.

The openings can be round such as holes or ellipses or football shapes, conical shapes with rounded bases, or polygonal shapes or any other shape, provided that the theoretical internal diameter of each opening is more than the particle size of the dry powder composition comprised in the intravaginal formulation.

Preferably the elongated tube is not more than 15 cm. The elongated tube can be single or multiple use. The elongated tube may be made of, but not limited to metal, polyethylene, polypropylene, cyclic olefins, polyethylene terephthalate, polyethylene terephthalate G and plasticized chloride among others or mixtures thereof and can be an unattachable part of the housing or adaptable to be attached to the housing. A suitably adaptable disposable/single use cap may be used for hygiene purposes to the multi-use elongated tubes.

With reference to the drawings, the structure and operation of the various components of the apparatus suitable for delivery of the intravaginal formulation, may be understood.

Figure 2:
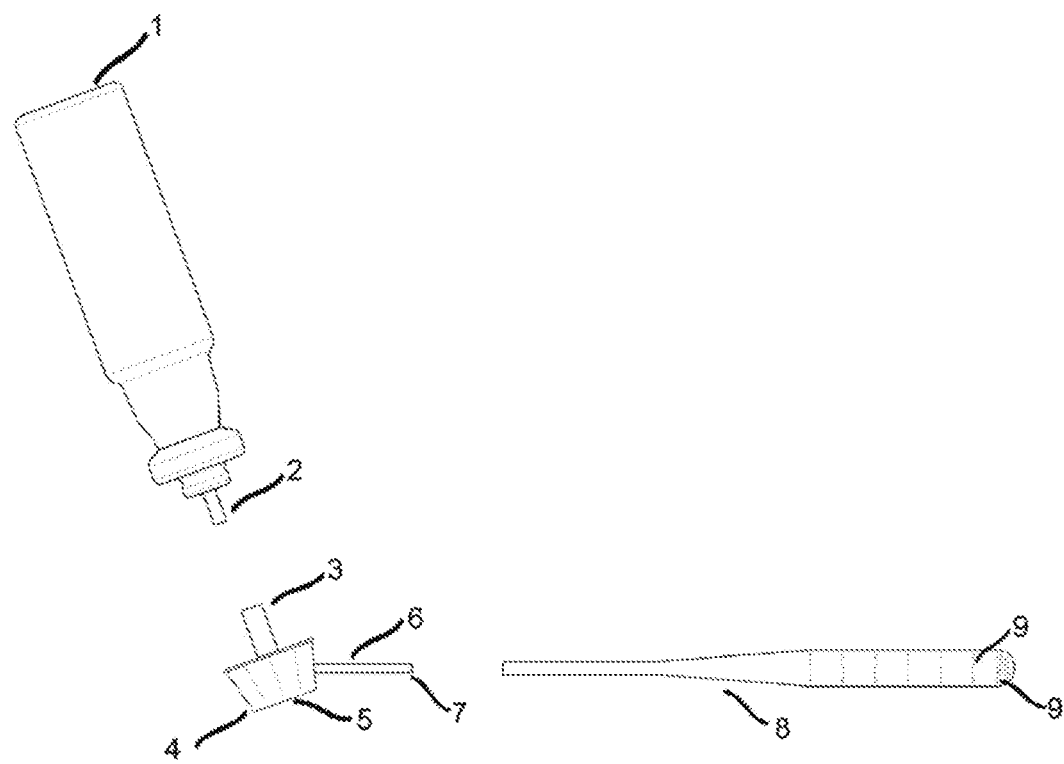
FIG. 2. An exploded perspective view of the assembling of FIG. 1.
Figure 5:
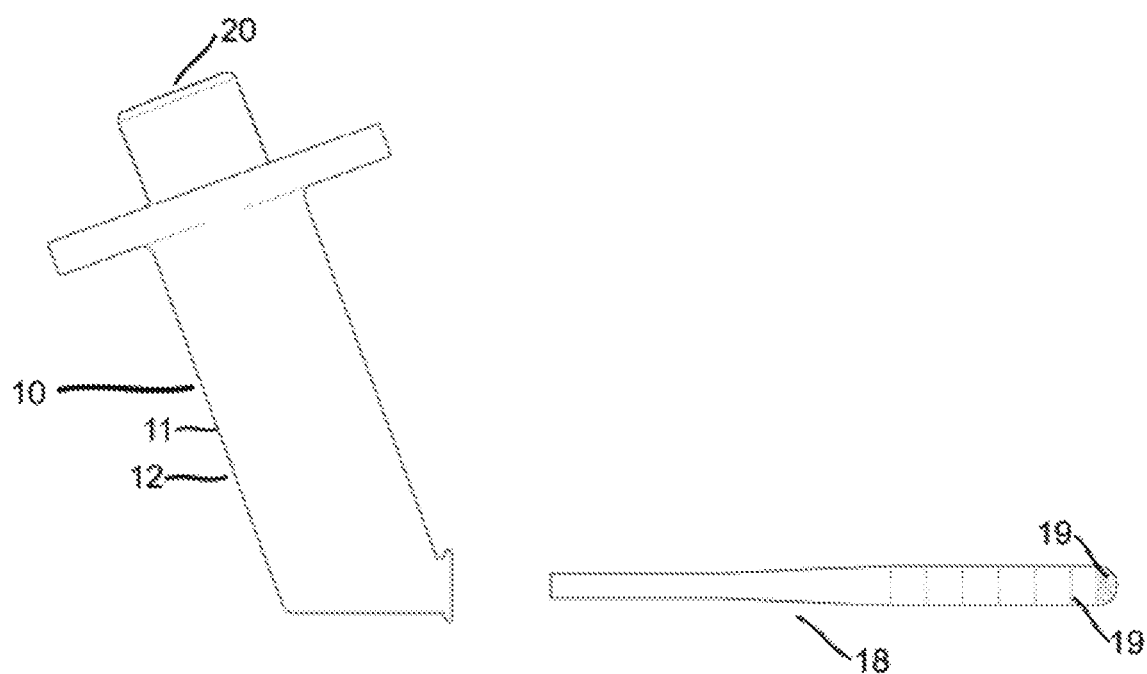
FIG. 5. An exploded perspective view of the assembling of FIG. 3, according to the present invention.

In the first embodiment of the apparatus of the intravaginal formulation (1), shown in FIG. 2, comprises an elongated tube/applicator probe (8) at least partially covered with openings (9) for dispensing the intravaginal formulation from the pressurized container (1) into the vagina, said elongated tube/applicator probe (8) having a closed end and an open end suitable to connect to the cap lip portion (6) at the open end for connection to the spray orifice of a valve operating spray nozzle of the container, said cap (4) having a spray actuator (5) for the container tip (2) to dispense the intravaginal formulation under pressure from the container, operable by actuating the spray actuator (5) of the container to dispense the dry powder composition.

In the second embodiment, the apparatus of the intravaginal formulation (10), shown in FIG. 3, comprises an elongated tube/applicator probe (18) at least partially covered with openings (19) for dispensing the intravaginal formulation from the pressurized container (20) into the vagina, said elongated tube elongated tube/applicator probe (18) having a closed end and an open end suitable to connect to closed end/wall of the tubular body (14) though a suitable sliding fit position and the product release chamber (16) formed by a housing (11) with handles on the open end (13) suitable for introducing the pressurized container (20) and a closed end/wall of the tubular body (14) wherein the application probe (18) is attached.

Figure 6:
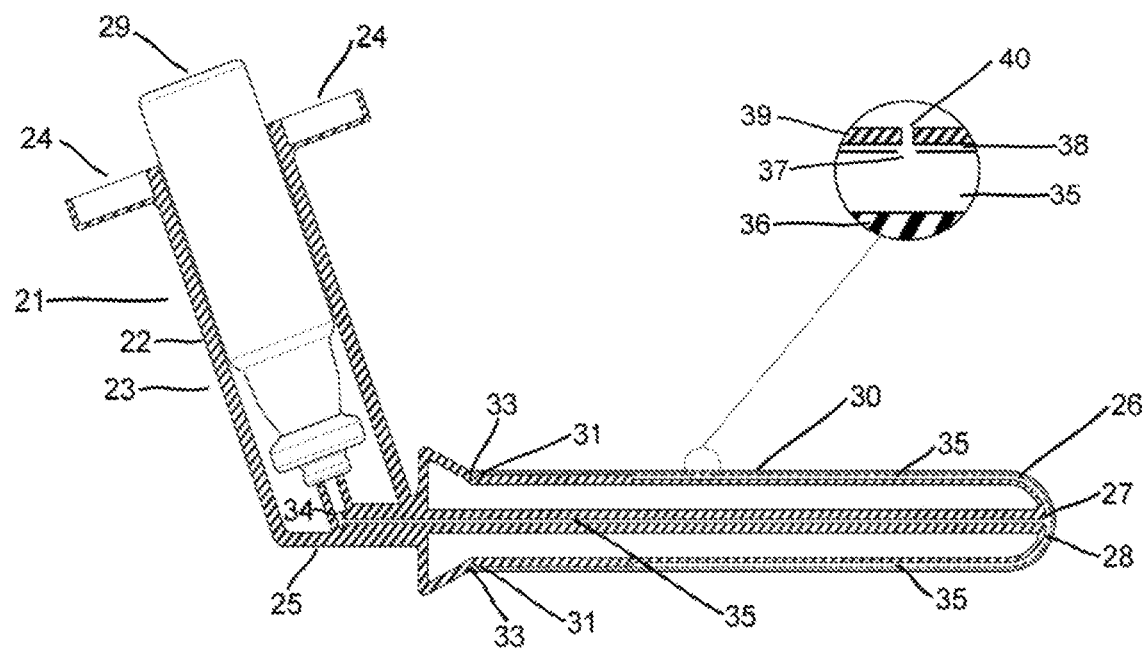
FIG. 6. A side cross-sectional view of an apparatus suitable for intravaginal delivery comprising a housing and a fixed tubular application piece, according to the present invention.
Figure 7:
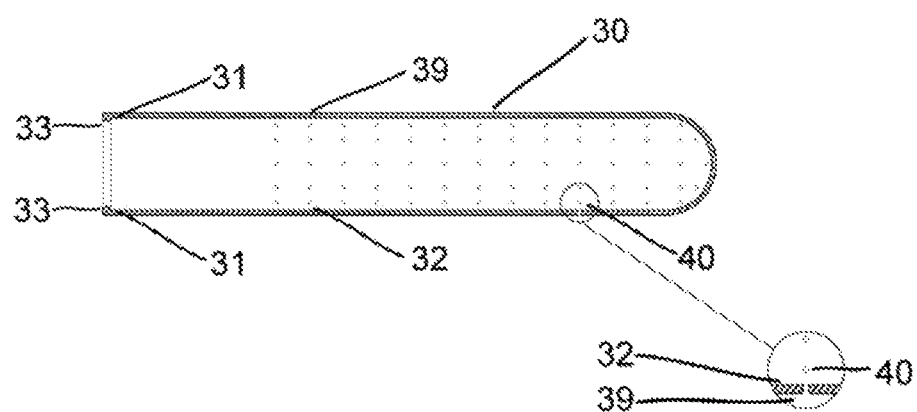
FIG. 7. A side view of the single-use cap with openings of FIG. 6.

In a third embodiment the apparatus of the intravaginal formulation (21), shown in FIG. 6, comprises a housing (22) with handles on the open end (24) suitable for introducing the pressurized container (29) and a closed end/wall of the tubular body (25) with an elongated tubular applicator piece (26) comprising openings with an tubular lip portion (27) having an external lip surface in contact with a suitable cap (30) and openings (40), suitably oriented, adaptable and attachable to the elongated tubular applicator (26) with openings (37) by snap-fit positions (33), capable to deliver the formulation through the openings (40) into the vagina after being simultaneously trapped in the channels of the chamber for product dispersing (35) as shown in an enlargement of FIG. 6.

Figure 8:
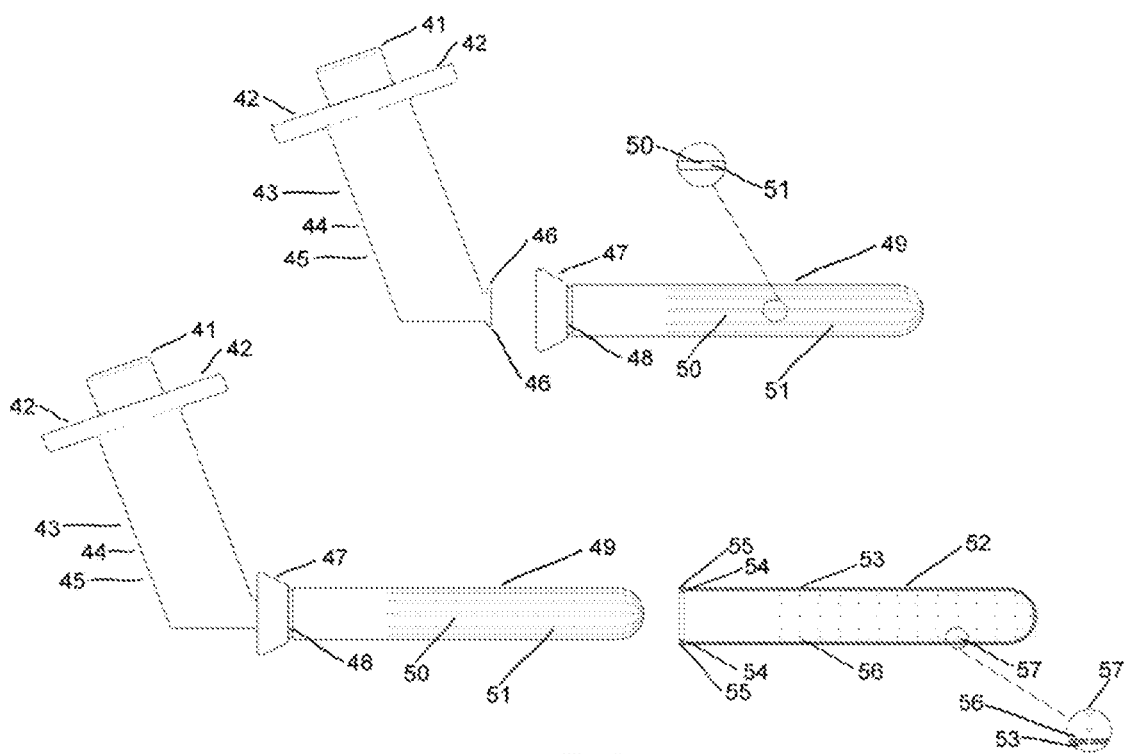
FIG. 8. An exploded perspective view of an apparatus with a fit positioned multi-use elongated tube and suitable single-use cap with openings, according to the present invention.

In a forth embodiment shown in FIG. 8, like FIG. 6 embodiment, the applicator tube (49) is attachable to the housing (44) with fit position (46).

Figure 9:
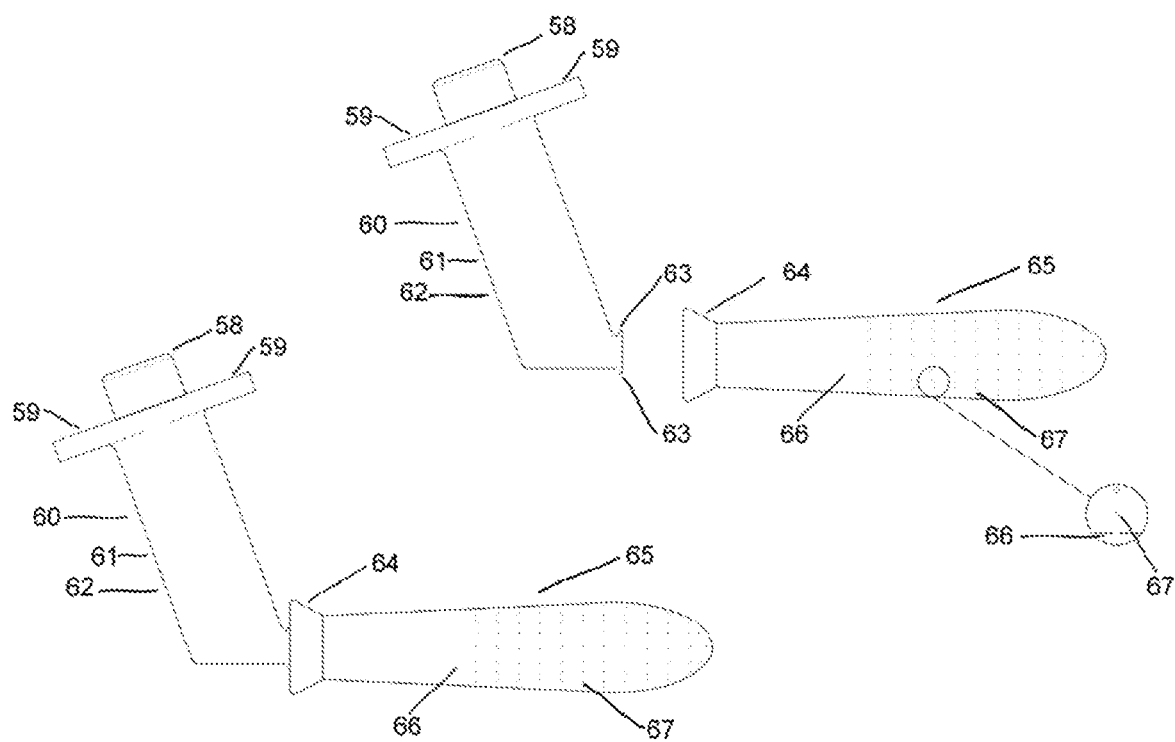
FIG. 9. An exploded perspective view of an apparatus with a fit positioned multi-use elongated tube without a cap, according to the present invention.

In a fifth embodiment of the apparatus (60), shown in FIG. 9, comprises an elongated tube/applicator probe (65) at least partially covered with openings (67) for dispensing the intravaginal formulation from the pressurized container (58) into the vagina, said elongated tube elongated tube/applicator probe (65) having a closed end and an open end (64) suitable to connect to closed end/wall of the tubular body (62) though a suitable fit position (63).

EXAMPLES

Example 1

Composition containing Metronidazole base and Boric Acid with HFA 134a as propellant gas.

TABLE 1

| Batch manufacturing formula: Example 1 | | | |
|---|---|---|---|
| Ingredients | mg/dose | Percentage % (without propellant) | Percentage % (with propellant) |
| API | | | |
| Metronidazole base | 37.50 | 10.6 | 0.5 |
| Excipients | | | |
| Boric Acid | 300.00 | 85.1 | 4.1 |
| Polycarbophil | 5.00 | 1.4 | 0.1 |
| Carbomer 974 | 10.00 | 2.8 | 0.1 |
| HFA 134a | 7050.00 | n/a | 95.2 |
| Total mass without propellant (mg) | 352.50 | | |
| Total percentage % | | 100.0 | 100.0 |
| Total mass with propellant (mg) | 7402.50 | | |

Brief Manufacturing Process Description:

Step 1: Weighing of all solid materials.

Step 2: Metronidazole and Boric Acid are dry mixed together in suitable mixer, until a homogenous powder mixture is obtained.

Step 3: The dry powder mixture of Step 2 wherein more than 90% of the total amount by volume of the particles have a size of more than 150 μm, is transferred into a milling or sizing device, set to size the dry mixture into a desired particle size, preferably below 50 μm and the yield is weighed.

Note: If Metronidazole and Boric Acid present a particle size more than 90% of the total amount by volume preferably below 50 μm, Steps 3 is skipped.

Step 4: Adding Carbomer 974 and Polycarbophil into the dry powder mixture of Step 2 or 3 and all materials are mixed together in a suitable mixer until a homogenous powder mixture is obtained.

Step 5: The appropriate quantity of the final powder mixture of Step 4 is loaded into pressurized containers and HFA 134a is inserted under a predetermined constant pressure.

Step 6: The pressurized containers are sealed under the same pressure applied in the system.

Example 2

Composition containing Metronidazole base and Boric Acid with n-pentane as propellant gas.

TABLE 2

Batch manufacturing formula: Example 2

| Ingredients | mg/dose | Percentage % (without propellant) | Percentage % (with propellant) |
| --- | --- | --- | --- |
| API | | | |
| Metronidazole base | 37.50 | 10.6 | 0.5 |
| Excipients | | | |
| Boric Acid | 300.00 | 85.1 | 4.1 |
| Polycarbophil | 5.00 | 1.4 | 0.1 |
| Carbomer 974 | 10.00 | 2.8 | 0.1 |
| n-pentane | 7050.00 | n/a | 95.2 |
| Total mass without propellant (mg) | 352.50 | | |
| Total percentage % | | 100.0 | 100.0 |
| Total mass with propellant (mg) | 7402.50 | | |

Brief Manufacturing Process Description:

Step 1: Weighing of all solid materials.

Step 2: Metronidazole and Boric Acid are dry mixed together in suitable mixer, until a homogenous powder mixture is obtained.

Step 3: The dry powder mixture of Step 2 wherein more than 90% of the total amount by volume of the particles have a size of more than 150 μm, is transferred into a milling or sizing device, set to size the dry mixture into a desired particle size, preferably below 50 μm and the yield is weighed.

Note: If Metronidazole and Boric Acid present a particle size more than 90% of the total amount by volume preferably below 50 μm, Steps 3 is skipped.

Step 4: Adding Carbomer 974 and Polycarbophil into the dry powder mixture of Step 2 or 3 and all materials are mixed together in a suitable mixer until a homogenous powder mixture is obtained.

Step 5: The appropriate quantity of the final powder mixture of Step 4 is loaded into pressurized containers and n-pentane is inserted under a predetermined constant pressure.

Step 6: The pressurized containers are sealed under the same pressure applied in the system.

Example 3

Composition containing Metronidazole base and Dequalinium Chloride with HFA 134a as propellant gas.

TABLE 3

Batch manufacturing formula: Example 3

| Ingredients | mg/dose | Percentage % (without propellant) | Percentage % (with propellant) |
| --- | --- | --- | --- |
| API | | | |
| Metronidazole base | 37.50 | 60.0 | 2.9 |
| Dequalinium Chloride | 10.00 | 16.0 | 0.8 |
| Excipients | | | |
| Polycarbophil | 5.00 | 8.0 | 0.4 |
| Carbomer 974 | 10.00 | 16.0 | 0.8 |
| HFA 134a | 1250.00 | n/a | 95.2 |
| Total mass without propellant (mg) | 62.50 | | |
| Total percentage % | | 100.0 | 100.0 |
| Total mass with propellant (mg) | 1312.50 | | |

Brief Manufacturing Process Description:

Step 1: Weighing of all solid materials.

Step 2: Metronidazole and Dequalinium Chloride are dry mixed together in suitable mixer, until a homogenous powder mixture is obtained.

Step 3: The dry powder mixture of Step 2 wherein more than 90% of the total amount by volume of the particles have a size of more than 150 μm, is transferred into a milling or sizing device, set to size the dry mixture into a desired particle size, preferably below 50 μm and the yield is weighed.

Note: If Metronidazole and Dequalinium Chloride present a particle size more than 90% of the total amount by volume preferably below 50 μm, Step 3 is skipped.

Step 4: Adding Carbomer 974 and Polycarbophil into the dry powder mixture of Step 2 or 3 and all materials are mixed together in a suitable mixer until a homogenous powder mixture is obtained.

Step 5: The appropriate quantity of the final powder mixture of Step 4 is loaded into pressurized containers and HFA 134a is inserted under a predetermined constant pressure.

Step 6: The pressurized containers are sealed under the same pressure applied in the system.

Example 4

Composition containing Metronidazole base and Dequalinium Chloride with n-pentane as propellant gas.

TABLE 4

Batch manufacturing formula: Example 4

| Ingredients | mg/dose | Percentage % (without propellant) | Percentage % (with propellant) |
|---|---|---|---|
| API | | | |
| Metronidazole base | 37.50 | 60.0 | 2.9 |
| Dequalinium Chloride | 10.00 | 16.0 | 0.8 |
| Excipients | | | |
| Polycarbophil | 5.00 | 8.0 | 0.4 |
| Carbomer 974 | 10.00 | 16.0 | 0.8 |
| n-pentane | 1250.00 | n/a | 95.2 |
| Total mass without propellant (mg) | 62.50 | | |
| Total percentage % | | 100.0 | 100.0 |
| Total mass with propellant (mg) | 1312.50 | | |

Brief Manufacturing Process Description:

Step 1: Weighing of all solid materials.

Step 2: Metronidazole and Dequalinium Chloride are dry mixed together in suitable mixer, until a homogenous powder mixture is obtained.

Step 3: The dry powder mixture of Step 2 wherein more than 90% of the total amount by volume of the particles have a size of more than 150 µm, is transferred into a milling or sizing device, set to size the dry mixture into a desired particle size, preferably below 50 µm and the yield is weighed.

Note: If Metronidazole and Dequalinium Chloride present a particle size more than 90% of the total amount by volume preferably below 50 µm, Step 3 is skipped.

Step 4: Adding Carbomer 974 and Polycarbophil into the dry powder mixture of Step 2 or 3 and all materials are mixed together in a suitable mixer until a homogenous powder mixture is obtained.

Step 5: The appropriate quantity of the final powder mixture of Step 4 is loaded into pressurized containers and n-pentane is inserted under a predetermined constant pressure.

Step 6: The pressurized containers are sealed under the same pressure applied in the system.

Example 5

Composition containing Boric Acid with HFA 134a as propellant gas.

TABLE 5

Batch manufacturing formula: Example 5

| Ingredients | mg/dose | Percentage % (without propellant) | Percentage % (with propellant) |
|---|---|---|---|
| API | | | |
| Boric Acid | 300.00 | 95.2 | 4.1 |
| Excipients | | | |
| Polycarbophil | 5.00 | 1.6 | 0.1 |
| Carbomer 974 | 10.00 | 3.2 | 0.1 |
| HFA 134a | 7050.00 | n/a | 95.7 |
| Total mass without propellant (mg) | 62.50 | | |
| Total percentage % | | 100.0 | 100.0 |
| Total mass with propellant (mg) | 7365.00 | | |

Brief Manufacturing Process Description:

Step 1: Weighing of all solid materials.

Step 2: Boric Acid wherein more than 90% of the total amount by volume of the particles have a size of more than 150 µm, is transferred into a milling or sizing device, set to size it to a desired particle size, preferably below 50 µm and the yield is weighed.

Note: If Boric Acid presents a particle size more than 90% of the total amount by volume preferably below 50 µm, Step 2 is skipped.

Step 3: Adding Carbomer 974 and Polycarbophil into the sized Boric Acid of Step 2 or added directly and all materials are mixed together in a suitable mixer until a homogenous powder mixture is obtained.

Step 4: The appropriate quantity of the final powder mixture of Step 3 is loaded into pressurized containers and HFA 134a is inserted under a predetermined constant pressure.

Step 5: The pressurized containers are sealed under the same pressure applied in the system.

Example 6

Composition containing Boric Acid with n-pentane as propellant gas.

TABLE 6

Batch manufacturing formula: Example 6

| Ingredients | mg/dose | Percentage % (without propellant) | Percentage % (with propellant) |
|---|---|---|---|
| API | | | |
| Boric Acid | 300.00 | 95.2 | 4.1 |
| Excipients | | | |
| Polycarbophil | 5.00 | 1.6 | 0.1 |
| Carbomer 974 | 10.00 | 3.2 | 0.1 |
| n-pentane | 7050.00 | n/a | 95.7 |
| Total mass without propellant (mg) | 62.50 | | |
| Total percentage % | | 100.0 | 100.0 |
| Total mass with propellant (mg) | 7365.00 | | |

Brief Manufacturing Process Description:

Step 1: Weighing of all solid materials.

Step 2: Boric Acid wherein more than 90% of the total amount by volume of the particles have a size of more than 150 μm, is transferred into a milling or sizing device, set to size it to a desired particle size, preferably below 50 μm and the yield is weighed.

Note: If Boric Acid presents a particle size more than 90% of the total amount by volume preferably below 50 μm, Step 2 is skipped.

Step 3: Adding Carbomer 974 and Polycarbophil into the sized Boric Acid of Step 2 or added directly and all materials are mixed together in a suitable mixer until a homogenous powder mixture is obtained.

Step 4: The appropriate quantity of the final powder mixture of Step 3 is loaded into pressurized containers and n-pentane is inserted under a predetermined constant pressure.

Step 5: The pressurized containers are sealed under the same pressure applied in the system.

Example 7

Composition containing Dequalinium Chloride with HFA 134a as propellant gas.

TABLE 7

Batch manufacturing formula: Example 7

| Ingredients | mg/dose | Percentage % (without propellant) | Percentage % (with propellant) |
|---|---|---|---|
| API | | | |
| Dequalinium Chloride | 10.00 | 40.0 | 0.8 |
| Excipients | | | |
| Polycarbophil | 5.00 | 20.0 | 0.4 |
| Carbomer 974 | 10.00 | 40.0 | 0.8 |
| HFA 134a | 1250.00 | n/a | 98.0 |
| Total mass without propellant (mg) | 25.00 | | |
| Total percentage % | | 100.0 | 100.0 |
| Total mass with propellant (mg) | 1275.00 | | |

Brief Manufacturing Process Description:

Step 1: Weighing of all solid materials.

Step 2: Dequalinium Chloride wherein more than 90% of the total amount by volume of the particles have a size of more than 150 μm, is transferred into a milling or sizing device, set to size it to a desired particle size, preferably below 50 μm and the yield is weighed.

Note: If Dequalinium Chloride presents a particle size more than 90% of the total amount by volume preferably below 50 μm, Step 2 is skipped.

Step 3: Adding Carbomer 974 and Polycarbophil into the sized Dequalinium Chloride of Step 2 or added directly and all materials are mixed together in a suitable mixer until a homogenous powder mixture is obtained.

Step 4: The appropriate quantity of the final powder mixture of Step 3 is loaded into pressurized containers and HFA 134a is inserted under a predetermined constant pressure.

Step 5: The pressurized containers are sealed under the same pressure applied in the system.

Example 8

Composition containing Dequalinium Chloride with n-pentane as propellant gas.

TABLE 3

Batch manufacturing formula: Example 8

| Ingredients | mg/dose | Percentage % (without propellant) | Percentage % (with propellant) |
|---|---|---|---|
| API | | | |
| Dequalinium Chloride | 10.00 | 40.0 | 0.8 |
| Excipients | | | |
| Polycarbophil | 5.00 | 20.0 | 0.4 |
| Carbomer 974 | 10.00 | 40.0 | 0.8 |
| n-pentane | 1250.00 | n/a | 98.0 |
| Total mass without propellant (mg) | 25.00 | | |
| Total percentage % | | 100.0 | 100.0 |
| Total mass with propellant (mg) | 1275.00 | | |

Brief Manufacturing Process Description:

Step 1: Weighing of all solid materials.

Step 2: Dequalinium Chloride wherein more than 90% of the total amount by volume of the particles have a size of more than 150 μm, is transferred into a milling or sizing device, set to size it to a desired particle size, preferably below 50 μm and the yield is weighed.

Note: If Dequalinium Chloride presents a particle size more than 90% of the total amount by volume preferably below 50 μm, Step 2 is skipped.

Step 3: Adding Carbomer 974 and Polycarbophil into the sized Dequalinium Chloride of Step 2 or added directly and all materials are mixed together in a suitable mixer until a homogenous powder mixture is obtained.

Step 4: The appropriate quantity of the final powder mixture of Step 3 is loaded into pressurized containers and n-pentane is inserted under a predetermined constant pressure.

Step 5: The pressurized containers are sealed under the same pressure applied in the system.

Example 9

Composition containing Metronidazole base with HFA 134a as propellant gas.

TABLE 9

Batch manufacturing formula:
Example 9

| Ingredients | mg/dose | Percentage % (without propellant) | Percentage % (with propellant) |
|---|---|---|---|
| API | | | |
| Metronidazole base | 37.50 | 71.4 | 3.4 |
| Excipients | | | |
| Polycarbophil | 5.00 | 9.5 | 0.5 |
| Carbomer 974 | 10.00 | 19.0 | 0.9 |
| HFA 134a | 1050.00 | n/a | 95.2 |
| Total mass without propellant (mg) | 52.50 | | |
| Total percentage % | | 100.0 | 100.0 |
| Total mass with propellant (mg) | 1102.50 | | |

Brief Manufacturing Process Description:

Step 1: Weighing of all solid materials.

Step 2: Metronidazole base wherein more than 90% of the total amount by volume of the particles have a size of more than 150 μm, is transferred into a milling or sizing device, set to size it to a desired particle size, preferably below 50 μm and the yield is weighed.

Note: If Metronidazole base presents a particle size more than 90% of the total amount by volume preferably below 50 μm, Step 2 is skipped.

Step 3: Adding Carbomer 974 and Polycarbophil into the sized Metronidazole base of Step 2 or added directly and all materials are mixed together in a suitable mixer until a homogenous powder mixture is obtained.

Step 4: The appropriate quantity of the final powder mixture of Step 3 is loaded into pressurized containers and HFA 134a is inserted under a predetermined constant pressure.

Step 5: The pressurized containers are sealed under the same pressure applied in the system.

Example 10

Composition containing Metronidazole base with n-pentane as propellant gas.

TABLE 10

Batch manufacturing formula:
Example 10

| Ingredients | mg/dose | Percentage % (without propellant) | Percentage % (with propellant) |
|---|---|---|---|
| API | | | |
| Metronidazole base | 37.50 | 71.4 | 3.4 |
| Excipients | | | |
| Polycarbophil | 5.00 | 9.5 | 0.5 |
| Carbomer 974 | 10.00 | 19.0 | 0.9 |
| n-pentane | 1050.00 | n/a | 95.2 |
| Total mass without propellant (mg) | 52.50 | | |
| Total percentage % | | 100.0 | 100.0 |
| Total mass with propellant (mg) | 1102.50 | | |

Brief Manufacturing Process Description:

Step 1: Weighing of all solid materials.

Step 2: Metronidazole base wherein more than 90% of the total amount by volume of the particles have a size of more than 150 μm, is transferred into a milling or sizing device, set to size it to a desired particle size, preferably below 50 μm and the yield is weighed.

Note: If Metronidazole base presents a particle size more than 90% of the total amount by volume preferably below 50 μm, Step 2 is skipped.

Step 3: Adding Carbomer 974 and Polycarbophil into the sized Metronidazole base of Step 2 or added directly and all materials are mixed together in a suitable mixer until a homogenous powder mixture is obtained.

Step 4: The appropriate quantity of the final powder mixture of Step 3 is loaded into pressurized containers and n-pentane is inserted under a predetermined constant pressure.

Step 5: The pressurized containers are sealed under the same pressure applied in the system.

Example 11

Composition containing Dequalinium Chloride, Polyquaternium 10 and Polyvinyl Alcohol.

TABLE 11

Batch manufacturing formula:
Example 11

| Ingredients | mg/dose | Percentage without propellant (%) | Percentage incl. propellant (%) |
|---|---|---|---|
| API | | | |
| Dequalinium Chloride | 10.00 | 45.45 | 0.79 |
| Excipients | | | |
| Polyquaternium 10 | 10.00 | 45.45 | 0.79 |
| Polyvinyl Alcohol n 500-5000 | 2.00 | 9.09 | 0.16 |
| HFA 134a | 1250.00 | n/a | 98.27 |
| Total mass of powder | 22.00 | 100.00 | 100.00 |

Brief Manufacturing Process Description:

Step 1: Weighing of all solid materials

Step 2: Dequalinium Chloride, Polyquaternium 10 and Polyvinyl Alcohol are dry mixed together in suitable mixer, until a homogenous powder mixture is obtained.

Step 3: The dry powder mixture of Step 2 wherein more than 90% of the total amount by volume of the particles have a size of more than 150 μm, is transferred into a milling or sizing device, set to size the dry mixture into a desired particle size, preferably below 50 μm and the yield is weighed.

Note: If Dequalinium Chloride, Polyquaternium 10 and Polyvinyl Alcohol present a particle size more than 90% of the total amount by volume preferably below 50 μm, Step 3 is skipped.

Step 4: The appropriate quantity of the powder mixture of Step 2 or 3 is loaded into pressurized containers and HFA 134a is inserted under a predetermined constant pressure.

Step 5: The pressurized containers are sealed under the same pressure applied in the system.

Example 12

Composition containing Dequalinium Chloride, Polycarbophil, various Carbomer grades and further fillers.

TABLE 12

Batch manufacturing formula: Example 12

| Ingredients | mg/dose | Percentage without propellant (%) | Percentage incl. propellant (%) |
|---|---|---|---|
| API | | | |
| Dequalinium Chloride | 10.00 | 22.22 | 0.77 |
| Excipients | | | |
| Polycarbophil | 5.00 | 11.11 | 0.39 |
| Carbomer 934 or 940 or 941 or 974 | 10.00 | 22.22 | 0.77 |
| Microcrystalline Cellulose | 10.00 | 22.22 | 0.77 |
| Lactose anhydrous | 10.00 | 22.22 | 0.77 |
| HFA 134a | 1250.00 | n/a | 96.53 |
| Total mass of powder | 45.00 | 100.00 | 100.00 |

Brief Manufacturing Process Description:

Step 1: Weighing of all solid materials

Step 2: Dequalinium Chloride, Microcrystalline Cellulose and Lactose anhydrous are dry mixed together in suitable mixer, until a homogenous powder mixture is obtained.

Step 3: The dry powder mixture of Step 2 wherein more than 90% of the total amount by volume of the particles have a size of more than 150 µm, is transferred into a milling or sizing device, set to size the dry mixture into a desired particle size, preferably below 50 µm and the yield is weighed.

Note: If Dequalinium Chloride, Microcrystalline Cellulose and Lactose anhydrous present a particle size more than 90% of the total amount by volume preferably below 50 µm, Step 3 is skipped.

Step 4: Adding Carbomer 934 or 940 or 941 or 974 and Polycarbophil into the sized dry mixture of Step 3 or added directly into the mixture of Step 2 and all materials are mixed together in a suitable mixer until a homogenous powder mixture is obtained.

Step 5: The appropriate quantity of the final powder mixture of Step 4 is loaded into pressurized containers and HFA 134a is inserted under a predetermined constant pressure.

Step 6: The pressurized containers are sealed under the same pressure applied in the system.

Example 13

Composition containing Dequalinium Chloride, Sodium Hyaluronate and Poloxamer.

TABLE 13

Batch manufacturing formula: Example 13

| Ingredients | mg/dose | Percentage without propellant (%) | Percentage incl. propellant (%) |
|---|---|---|---|
| API | | | |
| Dequalinium Chloride | 10.00 | 28.57 | 0.78 |
| Excipients | | | |
| Sodium Hyaluronate | 20.00 | 57.14 | 1.56 |
| Poloxamer 188 | 5.00 | 14.29 | 0.39 |
| HFA 134a | 1250.00 | n/a | 97.28 |
| Total mass of powder | 35.00 | 100.00 | 10.00 |

Brief Manufacturing Process Description:

Step 1: Weighing of all solid materials

Step 2: Dequalinium Chloride, Sodium Hyaluronate and Poloxamer 188 are dry mixed together in suitable mixer, until a homogenous powder mixture is obtained.

Step 3: The dry powder mixture of Step 2 wherein more than 90% of the total amount by volume of the particles have a size of more than 150 µm, is transferred into a milling or sizing device, set to size the dry mixture into a desired particle size, preferably below 50 µm and the yield is weighed.

Note: If Dequalinium Chloride, Sodium Hyaluronate and Poloxamer 188 present a particle size more than 90% of the total amount by volume preferably below 50 µm, Step 3 is skipped.

Step 4: The appropriate quantity of the final powder mixture of Step 2 or 3 is loaded into pressurized containers and HFA 134a is inserted under a predetermined constant pressure.

Step 5: The pressurized containers are sealed under the same pressure applied in the system.

Example 14

Composition containing Dequalinium Chloride, Acacia and Xanthan Gum.

TABLE 14

Batch manufacturing formula: Example 14

| Ingredients | mg/dose | Percentage without propellant (%) | Percentage incl. propellant (%) |
|---|---|---|---|
| API | | | |
| Dequalinium Chloride | 10.00 | 28.57 | 0.78 |
| Excipients | | | |
| Acacia | 15.00 | 42.86 | 1.17 |
| Xanthan Gum | 10.00 | 28.57 | 0.78 |
| HFA 134a | 1250.00 | n/a | 97.28 |
| Total mass of powder | 35.00 | 100.00 | 100.00 |

Brief Manufacturing Process Description:

Step 1: Weighing of all solid materials

Step 2: Dequalinium Chloride, Acacia and Xanthan gum are dry mixed together in suitable mixer, until a homogenous powder mixture is obtained.

Step 3: The dry powder mixture of Step 2 wherein more than 90% of the total amount by volume of the particles have a size of more than 150 µm, is transferred into a milling or sizing device, set to size the dry mixture into a desired particle size, preferably below 50 µm and the yield is weighed.

Note: If Dequalinium Chloride, Acacia and Xanthan gum present a particle size more than 90% of the total amount by volume preferably below 50 µm, Step 3 is skipped.

Step 4: The appropriate quantity of the final powder mixture of Step 2 or 3 is loaded into pressurized containers and HFA 134a is inserted under a predetermined constant pressure.

Step 5: The pressurized containers are sealed under the same pressure applied in the system.

Example 15

Composition containing Dequalinium Chloride, Polycarbophil and various Carbomer grades.

TABLE 15

Batch manufacturing formula:
Example 15

| Ingredients | mg/dose | Percentage without propellant (%) | Percentage incl. propellant (%) |
|---|---|---|---|
| API | | | |
| Dequalinium Chloride | 10.00 | 40.00 | 0.78 |
| Excipients | | | |
| Polycarbophil | 5.00 | 20.00 | 0.39 |
| Carbomer 934 or 940 or 941 or 974 | 10.00 | 40.00 | 0.78 |
| HFA 134a | 1250.00 | n/a | 98.04 |
| Total mass of powder | 25.00 | 100.00 | 100.00 |

Brief Manufacturing Process Description

Step 1: Weighing of all solid materials.

Step 2: Dequalinium Chloride wherein more than 90% of the total amount by volume of the particles have a size of more than 150 μm, is transferred into a milling or sizing device, set to size the dry mixture into a desired particle size, preferably below 50 μm and the yield is weighed.

Note: If Dequalinium Chloride presents a particle size more than 90% of the total amount by volume preferably below 50 μm, Step 2 is skipped.

Step 3: Adding Carbomer 934 or 940 or 941 or 974 and Polycarbophil into the sized Dequalinium Chloride of Step 2 or added directly and all materials are mixed together in a suitable mixer until a homogenous powder mixture is obtained.

Step 4: The appropriate quantity of the final powder mixture of Step 3 is loaded into pressurized containers and HFA 134a is inserted under a predetermined constant pressure.

Step 5: The pressurized containers are sealed under the same pressure applied in the system.

Example 16

Composition containing Dequalinium Chloride, and an anionic self emulsifier prepared by spray drying, in order to end up with a dry powder of the desired characteristics.

TABLE 16

Batch manufacturing formula:
Example 16

| Ingredients | mg/dose | Percentage without propellant (%) | Percentage incl. propellant (%) |
|---|---|---|---|
| API | | | |
| Dequalinium Chloride | 10.00 | 83.33 | 0.79 |
| Excipients | | | |
| Cetostearyl Alcohol Type B, emulsifying | 2.00 | 16.67 | 0.16 |
| Water, purified * | qs | n/a | n/a |
| HFA 134a | 1250.00 | n/a | 99.05 |
| Total mass of powder | 12.00 | 100.00 | 100.00 |

* Not present in the final product

Brief Manufacturing Process Description:

Step 1: Weighing of all solid materials

Step 2: Dequalinium Chloride is loaded for processing into the spray drier.

Step 3: Cetostearyl Alcohol Type B, emulsifying is dissolved in hot water and fed in the system.

Step 4: The process is executed and the material is simultaneously dried preferably below 5%, set to generate sprayed particles more than 90% of the total amount by volume preferably below 50 μm.

Step 5: If the obtained material of Step 4 presents a particle size more than 90% of the total amount by volume over 50 μm, then it is transferred into a milling or sizing device, set to size the dry mixture into a desired particle size, preferably below 50 μm.

Step 6: The appropriate quantity of the final powder mixture of Step 4 or 5 is loaded into containers and the HFA 134a is inserted under a predetermined constant pressure.

Step 6: The containers are sealed under the same pressure applied in the system.

Example 17

Composition containing Dequalinium Chloride, Sodium Hyaluronate, a glidant and a lubricant.

TABLE 17

Batch manufacturing formula:
Example 17

| Ingredients | mg/dose | Percentage without propellant (%) | Percentage incl. propellant (%) |
|---|---|---|---|
| API | | | |
| Dequalinium Chloride | 10.00 | 37.04 | 0.78 |
| Excipients | | | |
| Sodium Hyaluronate | 10.00 | 37.04 | 0.78 |
| Colloidal Silicon Dioxide | 5.00 | 18.52 | 0.39 |
| Magnesium Stearate | 2.00 | 7.41 | 0.15 |
| HFA 134a | 1250.00 | n/a | 97.28 |
| Total mass of powder | 27.00 | 100.00 | 100.00 |

Brief Manufacturing Process Description:

Step 1: Weighing of all solid materials.

Step 2: Dequalinium Chloride and Sodium Hyaluronate are dry mixed together in suitable mixer, until a homogenous powder mixture is obtained.

Step 3: The dry powder mixture of Step 2 wherein more than 90% of the total amount by volume of the particles have a size of more than 150 μm, is transferred into a milling or sizing device, set to size the dry mixture into a desired particle size, preferably below 50 μm and the yield is weighed.

Note: If Dequalinium Chloride and Sodium Hyaluronate present a particle size more than 90% of the total amount by volume preferably below 50 μm, Step 3 is skipped.

Step 4: Adding pre-sieved Colloidal Silicon Dioxide into the mixture of Step 2 or 3 and all materials are mixed together in a suitable mixer until a homogenous powder mixture is obtained.

Step 5: The mixture of Step 4 is lubricated using Magnesium Stearate.

Step 6: The appropriate quantity of the final powder mixture of Step 4 is loaded into pressurized containers and HFA 134a is inserted under a predetermined constant pressure.

Step 7: The pressurized containers are sealed under the same pressure applied in the system.

Example 18

Composition containing Dequalinium Chloride, Polycarbophil, various Carbomer grades and antioxidants.

TABLE 18

Batch manufacturing formula: Example 18

| Ingredients | mg/dose | Percentage without propellant (%) | Percentage incl. propellant (%) |
|---|---|---|---|
| API | | | |
| Dequalinium Chloride | 10.00 | 34.46 | 0.78 |
| Excipients | | | |
| Polycarbophil | 5.00 | 19.23 | 0.39 |
| Carbomer 934 or 940 or 941 or 974 | 10.00 | 34.46 | 0.78 |
| Butylated Hydroxyanisole | 2.00 | 1.92 | 0.04 |
| Butylated Hydroxytoluene | 2.00 | 1.92 | 0.04 |
| HFA 134a | 1250.00 | n/a | 97.96 |
| Total mass of powder | 26.00 | 100.00 | 100.00 |

Brief Manufacturing Process Description:

Step 1: Weighing of all solid materials.

Step 2: Dequalinium Chloride, Butylated Hydroxyanisole and Butylated Hydroxytoluene are dry mixed together in suitable mixer, until a homogenous powder mixture is obtained.

Step 3: The dry powder mixture of Step 2 wherein more than 90% of the total amount by volume of the particles have a size of more than 150 μm, is transferred into a milling or sizing device, set to size the dry mixture into a desired particle size, preferably below 50 μm and the yield is weighed.

Note: If Dequalinium Chloride Butylated Hydroxyanisole and Butylated Hydroxytoluene present a particle size more than 90% of the total amount by volume preferably below 50 μm, Step 3 is skipped.

Step 4: Adding Carbomer 934 or 940 or 941 or 974 and Polycarbophil into the mixture of Step 2 or 3 and all materials are mixed together in a suitable mixer until a homogenous powder mixture is obtained.

Step 5: The appropriate quantity of the final powder mixture of Step 4 is loaded into pressurized containers and HFA 134a is inserted under a predetermined constant pressure.

Step 6: The pressurized containers are sealed under the same pressure applied in the system.

Example 19

Composition containing Dequalinium Chloride and neutralizing agents.

TABLE 19

Batch manufacturing formula: Example 19

| Ingredients | mg/dose | Percentage without propellant (%) | Percentage incl. propellant (%) |
|---|---|---|---|
| API | | | |
| Dequalinium Chloride | 10.00 | 22.22 | 0.77 |
| Excipients | | | |
| Polycarbophil | 5.00 | 11.11 | 0.39 |
| Carbomer 934 or 940 or 941 or 974 | 10.00 | 22.22 | 0.77 |
| Lysine or Arginine or Histidine | 20.00 | 44.44 | 1.54 |
| HFA 134a | 1250.00 | n/a | 96.53 |
| Total mass of powder | 45.00 | 100.00 | 100.00 |

Brief Manufacturing Process Description:

Step 1: Weighing of all solid materials

Step 2: Dequalinium Chloride and Lysine or Arginine or Histidine are dry mixed together in suitable mixer, until a homogenous powder mixture is obtained.

Step 3: The dry powder mixture of Step 2 wherein more than 90% of the total amount by volume of the particles have a size of more than 150 μm, is transferred into a milling or sizing device, set to size the dry mixture into a desired particle size, preferably below 50 μm and the yield is weighed.

Note: If Dequalinium Chloride, Lysine or Arginine or Histidine present a particle size more than 90% of the total amount by volume preferably below 50 μm, Step 3 is skipped.

Step 4: The appropriate quantity of the final powder mixture of Step 2 or 3 is loaded into pressurized containers and HFA 134a is inserted under a predetermined constant pressure.

Step 5: The pressurized containers are sealed under the same pressure applied in the system.

Example 20

Composition containing Dequalinium Chloride, Mannitol and PEG 6000.

TABLE 20

Batch manufacturing formula: Example 20

| Ingredients | mg/dose | Percentage without propellant (%) | Percentage incl. propellant (%) |
|---|---|---|---|
| API | | | |
| Dequalinium Chloride | 10.00 | 20.00 | 0.77 |
| Excipients | | | |
| Polycarbophil | 5.00 | 10.00 | 0.38 |
| Carbomer 934 or 940 or 941 or 974 | 10.00 | 20.00 | 0.77 |
| Mannitol | 20.00 | 40.00 | 1.54 |
| Polyethylene Glycol 4000 or 6000 | 5.00 | 10.00 | 0.38 |
| HFA 134a | 1250.00 | n/a | 96.15 |
| Total mass of powder | 50.00 | 100.00 | 100.00 |

Brief Manufacturing Process Description:

Step 1: Weighing of all solid materials.

Step 2: Dequalinium Chloride and Polyethylene Glycol 4000 or 6000 are dry mixed together in suitable mixer, until a homogenous powder mixture is obtained.

Step 3: The dry powder mixture of Step 2 wherein more than 90% of the total amount by volume of the particles have a size of more than 150 µm, is transferred into a milling or sizing device, set to size the dry mixture into a desired particle size, preferably below 50 µm and the yield is weighed.

Note: If Dequalinium Chloride and Polyethylene Glycol 4000 or 6000 present a particle size more than 90% of the total amount by volume preferably below 50 µm, Step 3 is skipped.

Step 4: Adding a suitable grade of Mannitol (Mean diameter: 25 µm) and Carbomer 934 or 940 or 941 or 974 into the mixture of Step 2 or 3 and all materials are mixed together in a suitable mixer until a homogenous powder mixture is obtained.

Step 5: The appropriate quantity of the final powder mixture of Step 4 is loaded into pressurized containers and HFA 134a is inserted under a predetermined constant pressure.

Step 6: The pressurized containers are sealed under the same pressure applied in the system.

Example 21

Composition containing Dequalinium Chloride, various Carbomer grades and Dimethyl Ether.

TABLE 21

Batch manufacturing formula: Example 21

| Ingredients | mg/dose | Percentage without propellant (%) | Percentage incl. propellant (%) |
|---|---|---|---|
| API | | | |
| Dequalinium Chloride | 10.00 | 40.00 | 0.78 |
| Excipients | | | |
| Polycarbophil | 5.00 | 20.00 | 0.39 |
| Carbomer 934 or 940, or 941 or 974 | 10.00 | 40.00 | 0.78 |
| Dimethyl Ether | 1250.00 | n/a | 98.04 |
| Total mass of powder | 25.00 | 100.00 | 100.00 |

Brief Manufacturing Process Description:

Step 1: Weighing of all solid materials.

Step 2: Dequalinium Chloride wherein more than 90% of the total amount by volume of the particles have a size of more than 150 µm, is transferred into a milling or sizing device, set to size it to a desired particle size, preferably below 50 µm and the yield is weighed.

Note: If Dequalinium Chloride presents a particle size more than 90% of the total amount by volume preferably below 50 µm, Step 2 is skipped.

Step 3: Adding Carbomer 934 or 940 or 941 or 974 and Polycarbophil into the sized Dequalinium Chloride of Step 2 or added directly and all materials are mixed together in a suitable mixer until a homogenous powder mixture is obtained.

Step 4: The appropriate quantity of the final powder mixture of Step 3 is loaded into pressurized containers and dimethyl ether is inserted under a predetermined constant pressure.

Step 5: The pressurized containers are sealed under the same pressure applied in the system.

Example 22

Composition containing Dequalinium Chloride and non-liquified propellants.

TABLE 22

Batch manufacturing formula: Example 22

| Ingredients | mg/dose | Percentage without propellant (%) | Percentage incl. propellant (%) |
|---|---|---|---|
| API | | | |
| Dequalinium Chloride | 10.00 | 40.00 | 0.78 |
| Excipients | | | |
| Polycarbophil | 5.00 | 20.00 | 0.39 |
| Carbomer 934 or 940 or 941 or 974 | 10.00 | 40.00 | 0.78 |
| Compressed air or Carbon Dioxide or Nitrogen | 1250.00 | n/a | 98.04 |
| Total mass of powder | 25.00 | 100.00 | 100.00 |

Brief Manufacturing Process Description:

Step 1: Weighing of all solid materials.

Step 2: Dequalinium Chloride wherein more than 90% of the total amount by volume of the particles have a size of more than 150 µm, is transferred into a milling or sizing device, set to size it to a desired particle size, preferably below 50 µm and the yield is weighed.

Note: If Dequalinium Chloride presents a particle size more than 90% of the total amount by volume preferably below 50 µm, Step 2 is skipped.

Step 3: Adding Carbomer 934 or 940 or 941 or 974 and Polycarbophil into the sized Dequalinium Chloride of Step 2 or added directly and all materials are mixed together in a suitable mixer until a homogenous powder mixture is obtained.

Step 4: The appropriate quantity of the final powder mixture of Step 3 is loaded into pressurized containers and compressed air or carbon dioxide or nitrogen is inserted under a predetermined constant pressure.

Step 5: The pressurized containers are sealed under the same pressure applied in the system.

Example 23

Composition consisting of Dequalinium Chloride and propellant.

TABLE 23

Batch manufacturing formula: Example 23

| Ingredients | mg/dose | Percentage without propellant (%) | Percentage incl. propellant (%) |
|---|---|---|---|
| API | | | |
| Dequalinium Chloride | 10.00 | 100.00 | 0.79 |
| Excipients | | | |
| HFA 134a | 1250.00 | n/a | 99.21 |
| Total mass of powder | 10.00 | 100.00 | 0.79 |

Brief manufacturing process description:

Step 1: Weighing of the active ingredient.

Step 2: Dequalinium Chloride wherein more than 90% of the total amount by volume of the particles have a size of more than 150 μm, is transferred into a milling or sizing device, set to size it into a desired particle size, preferably below 50 μm and the yield is weighed.

Note: If Dequalinium Chloride presents a particle size more than 90% of the total amount by volume preferably below 50 μm, Step 2 is skipped.

Step 3: The appropriate quantity of the active ingredient from Step 1 or 2 is loaded into pressurized containers and HFA 134a is inserted under a predetermined constant pressure.

Step 4: The pressurized containers are sealed under the same pressure applied in the system.

Example 24

Composition prepared by various manufacturing processes well-known in the pharmaceutical industry that can be also applied, such as wet granulation, fluid bed granulation, freeze-drying and spray drying, in order to end up with a dry powder of the desired characteristics.

TABLE 24

Batch manufacturing formula: Example 24

| Ingredients | mg/dose | Percentage without propellant (%) | Percentage incl. propellant (%) |
|---|---|---|---|
| API | | | |
| Metronidazole base | 37.50 | 71.43 | 2.88 |
| Excipients | | | |
| Polyvinylpyrrolidone (PVP K-30) | 5.00 | 9.52 | 0.38 |
| Carbomer 934 or 940 or 941 or 974 | 10.00 | 19.05 | 0.77 |
| HFA 134a | 1250.00 | n/a | 95.97 |
| Water and/or suitable organic and/or inorganic solvent systems * | qs | n/a | n/a |
| Total mass of powder | 52.50 | 100.00 | 100.00 |

* Not present in the final product

Brief manufacturing process description:

Step 1: Weighing of all solid materials

Step 2: Metronidazole base is loaded for granulation processing (Fluid Bed granulator or granulator), along with Polyvinylpyrrolidone K-30 dissolved in the appropriate water and/or suitable organic and/or inorganic solvent system.

Step 3: The process is executed until a material of the desired characteristics occurs.

Step 4: The material is further on dried via suitable drying methods, preferably below 5%.

Step 5: The obtained material of Step 4 wherein more than 90% of the total amount by volume of the particles of the material have a size of of more than 150 μm, is transferred into a milling or sizing device, set to size the dry mixture into a desired particle size, preferably below 50 μm and the yield is weighed.

Note: If the obtained material of Step 4 presents a particle size more than 90% of the total amount by volume preferably below 50 μm, Step 5 is skipped.

Step 6: Adding Carbomer 934 or 940 or 941 or 974 into the dry powder mixture of Step 4 or 5 and all materials are mixed together in a suitable mixer until a homogenous powder mixture is obtained.

Step 7: The appropriate quantity of the final powder mixture of Step 6 is loaded into containers and the HFA 134a is inserted under a predetermined constant pressure.

Step 8: The containers are sealed under the same pressure applied in the system.

The invention claimed is:

1. An intravaginal formulation comprising at least one propellant and a dry powder composition comprising (i) at least one active agent for treatment of disease(s) associated with a vaginal tract and (ii) at least one thickening agent,
   wherein a moisture content of the intravaginal formulation is below 5% by weight with respect to the weight of the intravaginal formulation,
   wherein the intravaginal formulation does not comprise an organic or nonaqueous inorganic solvent system, and
   wherein the dry powder composition does not contain carrageenan, hypromellose or poloxamer thickening agent.

2. An intravaginal formulation according to claim 1, which comprises a chemical agent as the at least one active agent for treatment of disease(s) associated with the vaginal tract.

3. An intravaginal formulation according to claim 1, which comprises a biological agent as the at least one active agent for treatment of disease(s) associated with the vaginal tract.

4. An intravaginal formulation according to claim 1, wherein the dry powder composition further comprises an herbal extract.

5. An intravaginal composition according to claim 1, wherein the dry powder composition further comprises a pharmaceutically acceptable excipient.

6. An intravaginal formulation according to claim 1, wherein the moisture content of the dry powder composition is below 5%.

7. An intravaginal formulation according to claim 1, wherein more than 90% of the total amount by volume of the dry powder composition particles have a size of less than 150 μm, measured by laser diffraction analysis.

8. A method for treating a disease associated with a vagina comprising topically applying the intravaginal formulation of claim 1 to the vagina and/or female urogenital tract.

9. An intravaginal formulation according to claim 1, wherein the at least one active agent for treatment of disease(s) associated with the vaginal tract is selected from the group consisting of antibiotics, probiotics, prebiotics, pH-regulators, peptide/proteins, antibodies, vaccines and gene-based therapeutics.

10. An intravaginal formulation according to claim 1, wherein the at least one thickening agent is selected from the group consisting of acacia, agar, alginic acid, aliphatic polyesters, ammonium alginate, calcium alginate, sodium alginate, potassium alginate, arabic gum, attapulgite, bentonite, calcium polycarbophil, polyacrylic acid, ceratonia, cholesterol, copovidone, dextrins, dibutyl phthalate, dibutyl sebacate, diethyl phthalate, dimethyl phthalate, ethylene vinyl acetate, gelatin, glyceryl behenate, guar gum, hectorite, inulin, mucin, saponite, shellac, hyaluronic acid and its salts, pectin, polycarbophil polydextrose, polyethylene oxide, polyquaterniums, polyvinyl acetate, propylene glycol alginate, povidone, sulfobutyl ether β-cyclodextrin, tragacanth, trehalose, triacetin, xanthan gum, aluminum monostearate, cetostearyl alcohol, cetyl alcohol, stearyl alcohol, glyceryl monooleate, glyceryl palmitostearate, polyoxyethylene castor oils, polyoxyethylene stearates, polyoxyl glycerides, sorbitan fatty acid esters, and combinations thereof.

11. An intravaginal formulation comprising at least one propellant and a dry powder composition comprising (i) at least one active agent for treatment of disease(s) associated with a vaginal tract which is at least one hormone and (ii) at least one thickening agent,
   wherein a moisture content of the intravaginal formulation is below 5% by weight with respect to the weight of the intravaginal formulation, and
   wherein the dry powder composition does not contain carrageenan, hypromellose or poloxamer thickening agent.

12. An intravaginal formulation according to claim 11, wherein the intravaginal formulation does not comprise an organic or nonaqueous inorganic solvent system.

* * * * *